(12) United States Patent
Buseman et al.

(10) Patent No.: US 6,495,158 B1
(45) Date of Patent: Dec. 17, 2002

(54) ACNE PATCH

(75) Inventors: Teri Buseman, Minnetonka, MN (US); David Rolf, Eden Prairie, MN (US); Daniel M. McWhorter, Eagan, MN (US)

(73) Assignee: Lec Tec Corporation, Minnetonka, MN (US)

( * ) Notice: Subject to any disclaimer, the term of this patent is extended or adjusted under 35 U.S.C. 154(b) by 0 days.

(21) Appl. No.: 09/766,885

(22) Filed: Jan. 19, 2001

(51) Int. Cl.[7] .............................. A61K 7/00; A61K 9/70
(52) U.S. Cl. ...................... 424/443; 424/446; 424/448; 424/401
(58) Field of Search .................. 424/401, 448, 424/443, 446

(56) References Cited

U.S. PATENT DOCUMENTS

| | | | |
|---|---|---|---|
| 4,274,420 A | 6/1981 | Hymes | 128/641 |
| 4,307,717 A | 12/1981 | Hymes et al. | 128/156 |
| 4,355,028 A | 10/1982 | Kligman et al. | 424/230 |
| 4,446,145 A | 5/1984 | Van Bever | 424/273 R |
| 4,514,385 A | 4/1985 | Damani et al. | 424/81 |
| 4,675,009 A | 6/1987 | Hymes et al. | 604/304 |
| 4,696,854 A | 9/1987 | Ethier | 428/287 |
| 4,767,750 A | 8/1988 | Jacquet et al. | 514/159 |
| 5,137,923 A | 8/1992 | Philippe et al. | 514/859 |
| 5,258,421 A | 11/1993 | Lorenz et al. | 523/111 |
| 5,409,917 A | 4/1995 | Robinson et al. | 514/200 |
| 5,439,923 A | 8/1995 | Cullinan | 514/324 |
| 5,536,263 A | 7/1996 | Rolf et al. | 604/307 |
| 5,741,510 A | 4/1998 | Rolf et al. | 424/448 |
| 5,968,533 A | * 10/1999 | Porter et al. | 424/401 |
| 5,976,565 A | * 11/1999 | Fotinos | 424/448 |
| 6,096,333 A | 8/2000 | Rolf et al. | 424/443 |
| 6,096,334 A | 8/2000 | Rolf et al. | 424/443 |

FOREIGN PATENT DOCUMENTS

| | | | |
|---|---|---|---|
| EP | 0052705 | 6/1982 | A61K/31/455 |
| EP | 0563813 | 10/1993 | A61K/31/12 |
| GB | 1054124 | 1/1967 | A61K/3/84 |
| GB | 2088717 | 6/1982 | A61K/7/48 |
| GB | 2090135 | 7/1982 | A61K/7/48 |
| WO | 93/21899 | 11/1993 | A61K/7/48 |
| WO | WO0069405 | * 11/2000 | |

OTHER PUBLICATIONS

Sykes, N.L., et al., "Acne—A Review of Optimum Treatment", *Drugs*, 48, pp. 59–70, (1994).

* cited by examiner

*Primary Examiner*—Jos' G. Dees
*Assistant Examiner*—Mina Haghighatian
(74) *Attorney, Agent, or Firm*—Schwegman, Lundberg, Woessner & Kluth, P.A.

(57) ABSTRACT

An adhesive patch is provided wherein the patch includes a flexible backing having a front side and a back side. The patch also includes a therapeutic formulation positioned on and in at least a portion of the front side of the backing such that the therapeutic formulation is partially embedded in at least a portion of the front side of the backing. At least a portion of the backing is treated with a hydrophobic sizing agent such that the portion of the backing that is treated with the hydrophobic sizing agent has a surface energy of about 20 dynes/cm$^2$ to about 65 dynes/cm$^2$. The therapeutic formulation includes a topical acne drug, a solvent that dissolves the topical acne drug, and a pressure sensitive adhesive.

77 Claims, 5 Drawing Sheets

ACNE PATCH

BACKGROUND OF THE INVENTION

Acne vulgaris is a chronic disorder of the pilosebaceous follicles (apparatus) characterized by comedones (blackheads), papules, pustules, cysts, nodules, and often scars, that appear on the most visible areas of the skin (e.g., the face, chest, back, neck, and upper arms). The pilosebaceous apparatus is largely under the control of endogenous hormones (mainly androgens) which are present in unusually high concentrations in the blood during adolescence and puberty, giving rise to an excessive production of sebum. The condition may worsen by a simultaneous increase in the rate of keratinization of the skin's horny layer (the stratum comeum). As the horny cells proliferate, they can form an occlusive plug or comedone which coupled with the increased production of the sebum, represents an ideal medium for the proliferation of the skin resident strains, such as the Gram positive anaerobic bacterium, Propionibacterium acnes. Eventually, the plugged follicles rupture and allow the discharge of their contents, causing local swelling and inflammation. The exposed follicles may darken from the deposition of pigment from damaged cells in the deeper layer of skin. In severe cases, acne can lead to hospitalization of the patient, extensive discomfort, and long term scarring of the skin.

There are numerous treatments available for treating acne. Typically, acne is treated with topical formulations in the form of creams, gels, emulsions or lotions that contain selected agents. These agents include hormones or hormone agonists and antagonists (EP A1 0 563 813 and U.S. Pat. No. 5,439,923), antimicrobial agents (U.S. Pat. No. 4,446,145, GB 2,088,717, GB 2,090,135, GB 1,054,124, U.S. Pat. No. 5,409,917), salicylic acid (U.S. Pat. No. 4,514,385, U.S. Pat. No. 4,355,028, EP A1 0 052 705, FR-A 2,581,542, and FR-A 2,607,498). The problems associated with topical treatment of acne with creams, gels, emulsions and lotions include, e.g., the lack of precision of the application of the cream, gel, emulsion or lotions and the associated lack of control over precise doses to the target site. The application of a cream, gel, emulsion or lotion typically results in the exposure of an area considerably in excess of that covered by the acne, thereby exposing normal healthy skin to the anti-acne formulation. In addition, creams, gels, emulsions and lotions are messy and inconvenient.

Oral administration of anti-acne agents is currently provided for severe cases of acne. These are reviewed in "Acne, A Review of Optimum Treatment" by Sykes N. I. and Webster G. F in Drugs 48, 59–70 (1994). Numerous side-effects have been described using oral administration of anti-acne drugs. For example, isotretinoin, which is a derivative of vitamin A has associated risks of teratogenicity and may be a risk for women of childbearing age. Oral administration of antibiotics suited for treating acne may induce the appearance of adverse effects which include abdominal cramps, black tongue, cough, diarrhea, fatigue, irritation of the mouth and other undesirable symptoms.

Salicylic acid in the form of a tacky hydrophilic gel dressing (U.S. Pat. No. 5,258,421) and in combination with pantothenic acid or pantothenic acid derivative in a cleansing pad (PCT WO 93/21899) has been used for treating acne. In addition, a patch containing cephalosporin has been described in U.S. Pat. No. 5,409,917 for the treatment of acne using a method for making nicotine patches. Since the patch was not optimized for the special circumstances associated with acne including optimizing the anti-acne agent content and placement of the patch at multiple locations on exposed skin such as the face, the patch has not been adopted as an anti-acne formulation delivery modality.

FDA regulations (e.g., 21 C.F.R. Chapter 1, Section 333, Subpart D-Topical Acne Drug Products, Apr. 1, 2000 Edition) regulate what components (i.e., "active ingredients"), in a specified amount, may be described as treating acne (i.e., contains a topical acne drug). In order to follow FDA regulations, therefore, only a select number of active ingredients that are able to treat acne, in a specified amount, may be included in an adhesive patch when the patch is described as treating acne. Consequently, it is difficult to manufacture an adhesive patch that includes a topical acne drug, while at the same time maintaining (a) the solubility and stability of the active ingredients in the therapeutic formulation, (b) the pressure sensitive adhesive properties of the therapeutic formulation, and (c) following FDA regulations.

Several adhesive patches, drug dispensing devices, electrodes, and bandages have been disclosed for applying salicylic acid and/or sulfur to skin. See, e.g., U.S. Pat. Nos. 6,096,334; 6,096,033; 5,741,510; 5,536,263; 4,675,009; 4,307,717; and 4,274,420; which are all commonly assigned to Lec Tec Corporation. U.S. Pat. No. 4,274,420 discloses an electrode for use in monitoring and stimulation medical applications. The electrode includes a connector plug and a skin-interfacing substrate material. The substrate material can include salicylic acid in 17.8 wt. % (see, Example 2). The reference, however, does not disclose or suggest that the electrode can be used to treat acne. In addition, the reference does not disclose or suggest that salicylic acid can be present in the amount permitted by the FDA (e.g., 0.5 wt. % to 2.0 wt. % of the substrate). As such, the amount of salicylic acid disclosed therein does not comply with FDA regulations for topical acne drugs. See, 21 C.F.R. Chapter 1, Section 333, Subpart D- Topical Acne Drug Products, Apr. 1, 2000 Edition. Additionally, the backing is not disclosed as being treated with a sizing agent.

U.S. Pat. No. 4,307,717 discloses a bandage that includes a backing element and a substrate attached to the backing element. The substrate includes a matrix that includes a medicament. It is disclosed that the medicament can be a keratolytic agent such as salicylic acid or an antipruritic agent such as sulfur. However, the amount of salicylic acid or sulfur that can be employed in the matrix or substrate is not disclosed. The reference does not disclose or suggest that the bandage can be used to treat acne. In addition, the reference does not disclose or suggest that salicylic acid or sulfur can be present in the amount permitted by the FDA (e.g., 0.5 wt. % to 2.0 wt. % of the substrate or 3.0 wt. % to about 10.0 wt. % of the substrate, respectively). See, 21 C.F.R. Chapter 1, Section 333, Subpart D- Topical Acne Drug Products, Apr. 1, 2000 Edition. Additionally, the backing is not disclosed as being treated with a sizing agent.

U.S. Pat. No. 4,675,009 discloses a drug dispensing device (e.g., an adhesive skin reservoir) for the transdermal delivery of a medicament. The drug dispensing device includes a backing element and a substrate attached to the backing element. The substrate includes a medicament wherein the medicament can be a keratolytic agent such as salicylic acid (see, col. 3, line 66) or an antipruritic agent such as sulfur. The salicylic acid can be present in 8–20% of the substrate (see, Example 20). The amount of sulfur that can be employed in the substrate is not disclosed. The reference does not disclose or suggest that the drug dispensing device can be used to treat acne. In addition, the reference does not disclose or suggest that salicylic acid or sulfur can be present in the amount permitted by the FDA (e.g., 0.5 wt. % to 2.0 wt. % of the substrate or 3.0 wt. % to about 10.0 wt. % of the substrate, respectively). See, 21 C.F.R. Chapter 1, Section 333, Subpart D- Topical Acne Drug Products, Apr. 1, 2000 Edition. Additionally, the backing is not disclosed as being treated with a sizing agent.

U.S. Pat. Nos. 5,536,263 and 5,741,510 disclose an adhesive patch for applying medication to the skin. The patch includes a backing and a hydrocolloidal gel located on and in the backing. The gel includes a pressure-sensitive adhesive and a medicament. The medicament can be a keratolytic agent such as salicylic acid (see, col. 5, lines 35–36). The salicylic acid can be present in 4.1 wt. % (see, Example 46). The reference does not disclose or suggest that the adhesive patch can be used to treat acne. In addition, the reference does not disclose or suggest that salicylic acid can be present in the amount permitted by the FDA (e.g., 0.5 wt. % to 2.0 wt. % of the substrate). As such, the amount of salicylic acid disclosed therein does not comply with FDA regulations for topical acne drugs. See, 21 C.F.R. Chapter 1, Section 333, Subpart D- Topical Acne Drug Products, Apr. 1, 2000 Edition. Additionally, the backing is not disclosed as being treated with a sizing agent.

U.S. Pat. Nos. 6,096,333 and 6,096,334 disclose adhesive patches for applying medication to the skin. The patch includes a backing layer and a hydrophilic pressure-sensitive adhesive reservoir that includes a medicament. The medicament can be a keratolytic agent such as salicylic acid (see, col. 5, line 41). The salicylic acid can be present in 4.1 wt. % (see, Example 46). The references do not disclose or suggest that the adhesive patches can be used to treat acne. In addition, the references do not disclose or suggest that salicylic acid can be present in the amount permitted by the FDA (e.g., 0.5 wt. % to 2.0 wt. % of the substrate). As such, the amount of salicylic acid disclosed therein does not comply with FDA regulations for topical acne drugs. See, 21 C.F.R. Chapter 1, Section 333, Subpart D- Topical Acne Drug Products, Apr. 1, 2000 Edition. Additionally, the backing is not disclosed as being treated with a sizing agent.

The adhesive patches, drug dispensing devices, electrodes, and bandages disclosed in, e.g., U.S. Pat. Nos. 6,096,334; 6,096,033; 5,741,510; 5,536,263; 4,675,009; 4,307,717; and 4,274,420 have experienced success in applying and/or delivering medication to the skin. There exist several drawbacks, however, in the use of these adhesive patches, drug dispensing devices, electrodes, and bandages for delivering salicylic acid, in the amount permitted by the FDA, to treat acne or pimples. Specifically, the use of salicylic acid permitted by the FDA for acne medications has resulted in a less than desirable overall yield of product, a less than desirable "holdout" of therapeutic formulation on the backing, and a more than desirable degree of penetration of the therapeutic formulation in the backing.

U.S. Pat. No. 5,976,565 discloses a device for the topical treatment of acne. The device requires the presence of at least two agents suited for treating acne. See, e.g., col. 2, lines 36–37. The patch disclosed therein includes a release layer and at least one adhesive polymeric matrix layer located between the backing film and the release layer. As such, the adhesive polymeric matrix layer is not disclosed as being embedded or partially embedded in the backing film.

Many adhesive patches are manufactured or produced, for example, by mixing an ointment or gel in a mixer, then expelling the ointment or gel in a fluid state from the mixer onto the exposed front surface of a backing sheet. The fluid ointment or gel is then spread over the exposed surface of the backing sheet using an appropriate direct coating technique, such as knife-over-roll. This method of application allows the ointment or gel to penetrate a substantial portion of the backing sheet before it solidifies. However, if the fluid ointment or gel penetrates the backing too rapidly, it is possible for the ointment or gel to penetrate through the entire thickness of the backing before solidifying. Complete penetration of the ointment or gel through the backing results in the back side of the backing having a tacky surface. A tacky back side of the backing is unacceptable in that it may cause problems with further processing, such as die cutting or packaging, that is required to produce a finished product, and because it is an unattractive feature to the product consumer. Controlling the rate of penetration, such that the gel or ointment has solidified after it has begun to penetrate the backing, but before it has passed completely through the backing, or controlling the depth to which the ointment or gel will easily penetrate before solidifying, has been a persistent challenge.

There is a need therefore for methods and devices for treating patients with acne that have minimum adverse effects, have maximum efficacy, may be simple and comfortable to use, administers to the skin an effective and known amount of a topical acne drug, and complies with FDA regulations. The device will preferably be an adhesive patch that effectively controls the rate of penetration and/or effectively controls the depth to which the ointment or gel will penetrate before solidifying.

SUMMARY OF THE INVENTION

The present invention provides a water insoluble, protective, adhesive patch useful for treating or preventing acne or a pimple. The patch can prevent infections associated with acne or a pimple. The patch administers to the skin an effective and known amount of a topical acne drug. The patch maintains the adhesiveness of the adhesive and the stability of the topical acne drug over a prolonged period of time typically experienced in the manufacturing, packaging, shipping, and/or the storage of the patch. The topical acne drug, solvent, and pressure sensitive adhesive are positioned on at least a portion of the adhesive patch, in at least a portion of the adhesive patch, or on and in at least a portion of the adhesive patch. Preferably, the topical acne drug, solvent, and pressure sensitive adhesive are partially embedded in at least a portion of the adhesive patch. Additionally, the patch complies with FDA regulations (e.g., 21 C.F.R. Chapter 1, Section 333, Subpart D- Topical Acne Drug Products, Apr. 1, 2000 Edition). The adhesive patch of the present invention can include a gel that is not water-based. The adhesive patch includes a backing that is treated with a hydrophobic sizing agent (e.g., a fluorocarbon solution, silicone, or a combination thereof). The use of such backing prevents immediate wick through and maintains the hydrogel from penetrating the backing too quickly. In addition, the use of such backing provides a patch with a higher yield improvement and superior holdout properties. The use of such backing also obviates the need for a backing liner or a release liner. In such an embodiment, the adhesive patch can exist as a self wound adhesive patch.

The present invention provides an adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a hydrophobic sizing agent such that the portion of the backing that is treated with the hydrophobic sizing agent has a surface energy of about 20 dynes/cm$^2$ to about 65 dynes/cm$^2$. The therapeutic formulation includes a topical acne drug, a solvent that dissolves the topical acne drug, and a pressure sensitive adhesive.

The present invention also provides for another adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a hydrophobic sizing agent such that the portion of the backing treated with the hydrophobic sizing agent has a surface energy of about 20 dynes/cm$^2$ to about 65 dynes/cm$^2$. The therapeutic formulation includes salicylic acid or a pharmaceutically acceptable salt thereof present in about 0.5 wt. % to about 2.0 wt. % of the therapeutic formulation, a solvent that dissolves the salicylic acid, and a pressure sensitive adhesive.

The present invention also provides another adhesive patch. The adhesive patch includes a flexible backing having a front side and a back side. A therapeutic formulation is positioned on at least a portion of the front side of the backing, in at least a portion of the front side of the backing, or on and in at least a portion of the front side of the backing. At least a portion of the backing is treated with a hydrophobic sizing agent such that the portion of the backing treated with the hydrophobic sizing agent has a surface energy of about 20 dynes/cm$^2$ to about 65 dynes/cm$^2$. The therapeutic formulation includes a topical acne drug and a hot melt adhesive.

The therapeutic formulation can be partially embedded in at least a portion of the front side of the backing. The therapeutic formulation can be located on the entire surface of the front side of the backing. The backing can be porous. The backing can be vapor permeable. Upon contact with skin, the backing can retain the therapeutic formulation while the patch allows moisture from the skin to pass. The backing can include water insoluble material. The backing can have a thickness of about 0.025 mm to about 1.25 mm. The backing can include a nonwoven fabric. The backing can include polycellulose fibers, polyester fibers, polyurethane fibers, polyolefin fibers, polyamide fibers, cotton fibers, copolyester fibers, or any mixture thereof.

The hydrophobic sizing agent can be a fluorocarbon solution, a silicone-containing compound, or a combination thereof. The backing that is treated with the fluorocarbon solution can be Vilmed M1585 W/HY, Vilmed M1585H/HY, Vilmed M1586 W/HY, Vilmed M1586 H/HY, Vilmed M1570, Vilmed M 1573 F, Vilmed M 1573 FH, Vilmed M 1577 F, Vilmed M 1578 F, Vilmed M 1578 FH, or a combination thereof. The silicone-containing compound can be a polydimethyl siloxane, a dialkylsiloxane, a dimethylsiloxo vinyl alkene, a dialkylsiloxo vinyl alkene, a dimethylsiloxo acrylate, a dialkylsiloxo acrylate, a vinyl terminated polydimethylsiloxane, a vinyl terminated polydialkylsiloxane, or a combination thereof. At least a portion of the front side of the backing treated with the sizing agent. The entire surface of the front side of the backing can be treated with the sizing agent. The entire backing can be treated with the sizing agent. The sizing agent can be partially embedded in the backing.

The topical acne drug can be salicylic acid, resorcinol, resorcinol acetate, benzoyl peroxide, sulfur, retinol, retinoic acid, citric acid, an alpha hydroxy acid, retinal, a pharmaceutically acceptable salt thereof, or any combination thereof. The topical acne drug can be salicylic acid or a pharmaceutically acceptable salt thereof. The salicylic acid or the pharmaceutically acceptable salt thereof can be present in about 0.5 wt. % to about 2.0 wt. % of the therapeutic formulation. The sulfur can be present in about 3.0 wt. % to about 10.0 wt. % of the therapeutic formulation.

The solvent can include a polyhydric alcohol, water, or a combination thereof. The polyhydric alcohol can be propylene glycol, ethylene glycol, or a combination thereof. The propylene glycol can be present in about 3.0 wt. % to about 11.0 wt. % of the therapeutic formulation. The water can be present in about 2.0 wt. % to about 20.0 wt. % of the therapeutic formulation. The solvent can be present in about 6.0 wt. % to about 24.0 wt. % of the therapeutic formulation.

The therapeutic formulation can further include a filler. The filler can be malto dextrin. The malto dextrin can be present in about 1.0 wt. % to about 10.0 wt. % of the therapeutic formulation. The pressure sensitive adhesive can include one or more acrylic ester copolymers. The one or more acrylic ester copolymers can be present in about 3.0 wt. % to about 20.0 wt. % of the therapeutic formulation. The acrylic ester copolymer can be present in about 5.0 wt. % to about 15.0 wt. % of the therapeutic formulation. The adhesive can be positioned on the entire front side of the backing. The adhesive can be positioned on a portion of front side of the backing. The adhesive can be partially embedded in at least a portion of the backing.

The pressure sensitive adhesive can further include glycerin. The glycerin can be present in about 25.0 wt. % to about 70.0 wt. % of the therapeutic formulation. The glycerin can be present in about 45.0 wt. % to about 55.0 wt. % of the therapeutic formulation. The pressure sensitive adhesive can include an emulsifier. The emulsifier can be pectin. The pectin can be present in about 2.0 wt. % to about 10.0 wt. % of the therapeutic formulation.

The pressure sensitive adhesive can include a compound that provides structure and strength to the pressure sensitive adhesive or to the therapeutic formulation. The compound that provides structure and strength to the pressure sensitive adhesive or to the therapeutic formulation can be karaya, a polyacrylamide, xanthum gum, guar gum, a natural polymer, a synthetic polymer, a hydrophilic polymer, a hydrocolloidal polymer, starch, a starch derivative, vinyl acetate copolymer, polyvinyl pyrrolidone, polyethylene oxide, algin, derivatives of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS or a mixture thereof. The compound that provides structure and strength to the pressure sensitive adhesive or to the therapeutic formulation can be polyacrylamide. The polyacrylamide can be present in about 8.0 wt. % to about 30.0 wt. % of the therapeutic formulation. The compound that provides structure and strength to the pressure sensitive adhesive or to the therapeutic formulation can be karaya. The karaya can be present in about 8.0 wt. % to about 40.0 wt. % of the therapeutic formulation. The compound that provides structure and strength to the pressure sensitive adhesive or to the therapeutic formulation can be a combination of polyacrylamide and karaya.

The pressure sensitive adhesive can be located on the entire portion of the front side of the backing. The therapeutic formulation can further include a skin conditioner. The skin conditioner can be calamine, aloe, lanolin, glycerin, Vitamin E, Vitamin E acetate, farnesol, glycyrrhetinic acid, or any combination thereof. The aloe can be present in about 0.01 wt. % to about 2.0 wt. % of the therapeutic formulation. The Vitamin E acetate can be present in about 0.01 wt. % to about 2.0 wt. % of the therapeutic formulation.

The therapeutic formulation can further include one or more antimicrobial agents. The antimicrobial agent can be a β-lactam compound, an aminoglycoside, or an antifungal agent. The antimicrobial agent can be erythromycin, tetracycline, clindamycin, or cephalosporin. The therapeutic formulation can further include one or more antiseptic agents. The antiseptic agent can be triclosan, phenoxy isopropanol, chlorhexidine gluconate, povidone iodine, or any combination thereof.

The adhesive patch can have a thickness of about 0.20 mm to about 0.75 mm. The adhesive patch can further include a release liner that is mounted on the front side of the backing. More than one patch can be mounted on the release liner. About 2 to about 20 adhesive patches are mounted on the release liner. The adhesive patch can be crescent, circular, or oval. The adhesive patch can have a diameter of about 0.1 inch to about 1.0 inch.

The portion of the backing treated with the hydrophobic sizing agent can have a surface energy of about 27 dynes/cm$^2$ to about 56 dynes/cm$^2$. The entire surface of the backing can be treated with the hydrophobic sizing agent. The hydrophobic sizing agent can penetrate at least a portion of the underlying surface of the backing. The hydrophobic sizing agent can penetrate the entire underlying surface of the backing.

The present invention also provides a method for treating or preventing acne or a pimple in a mammal (e.g., human) in need thereof. The method includes applying to the skin surface of the mammal having the acne or the pimple or the skin surface of the mammal at risk thereof an adhesive patch of the present invention for an effective period of time effective to treat or prevent acne or a pimple. The skin surface of the mammal having the acne or pimple or the skin surface of the mammal at risk thereof can be the face, neck, shoulder, chest, back, or any combination thereof. The effective period of time can be about one hour to about 12 hours.

The present invention also provides a method for exfoliating the skin surface of a mammal (e.g., human). The method includes applying to the skin surface of the mammal in need of such exfoliation an adhesive patch of the present invention. The adhesive patch is applied for an effective period of time after which the adhesive patch is removed, thereby effectively exfoliating the skin surface. The effective period of time can be about one second to about 12 hours.

DETAILED DESCRIPTION OF THE INVENTION

Figure 1:
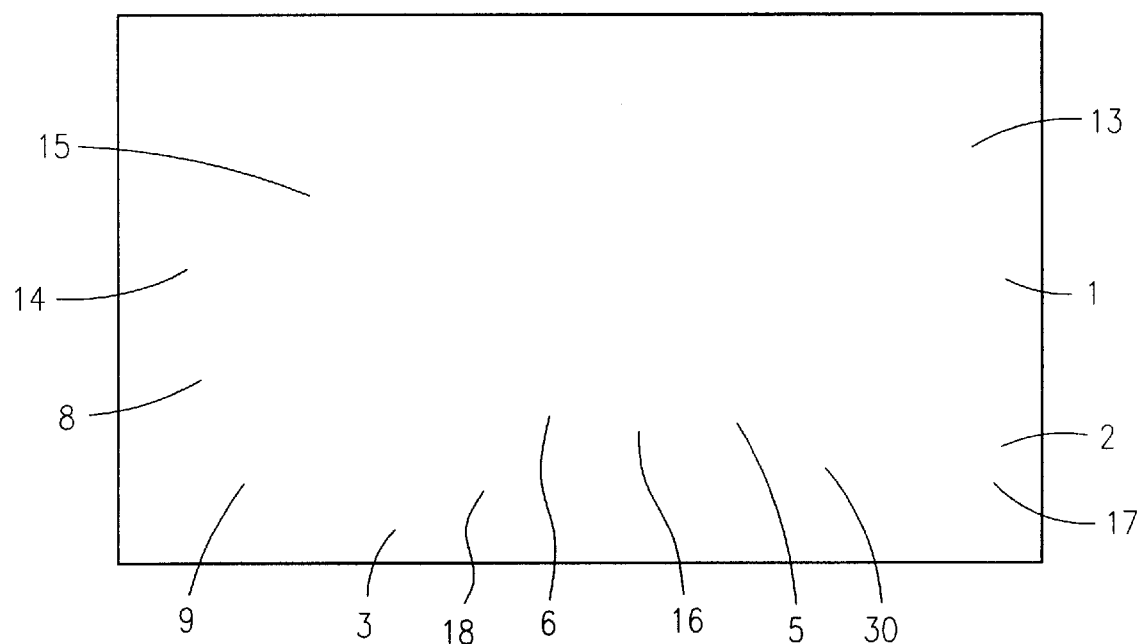
FIG. 1 illustrates the front side of an adhesive patch of the present invention.
Figure 2:
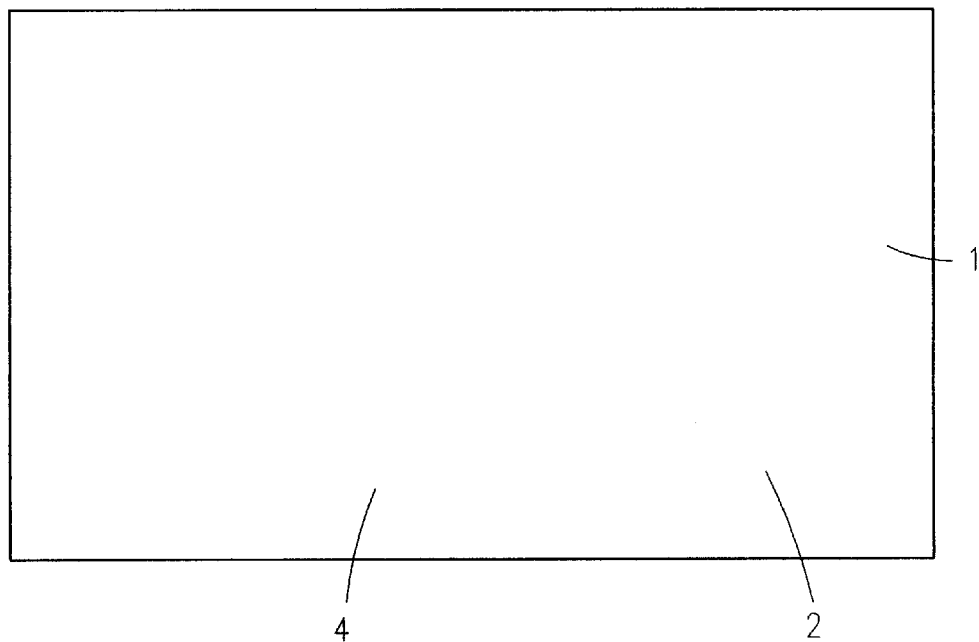
FIG. 2 illustrates the back side of an adhesive patch of the present invention.
Figure 3:
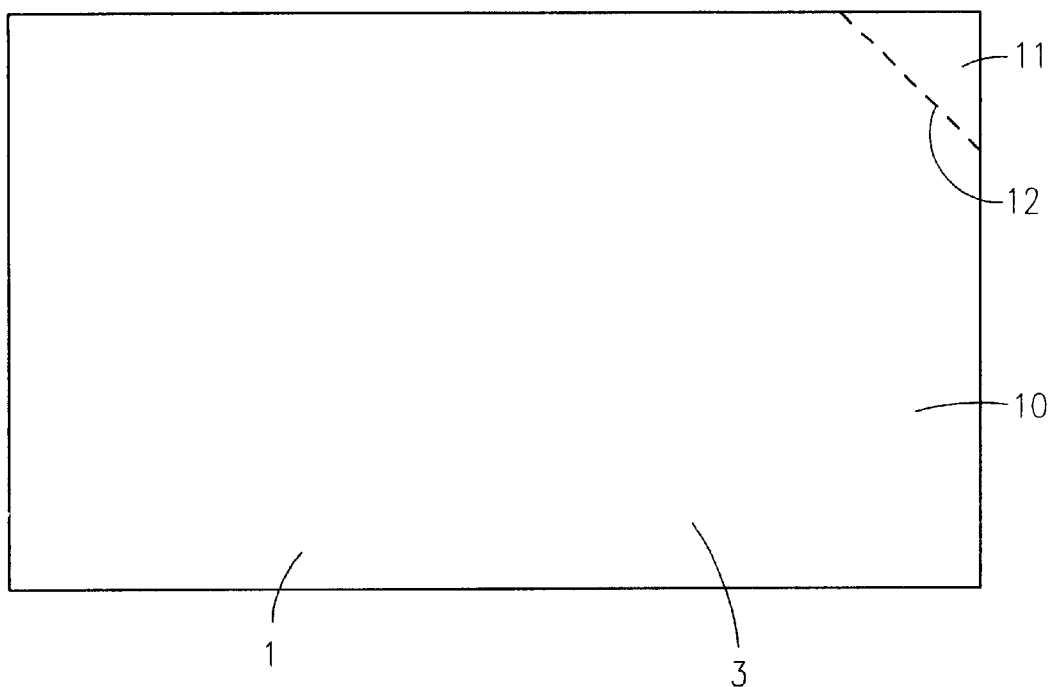
FIG. 3 illustrates the front side of an adhesive patch of the present invention with a release liner attached to the patch.
Figure 4:
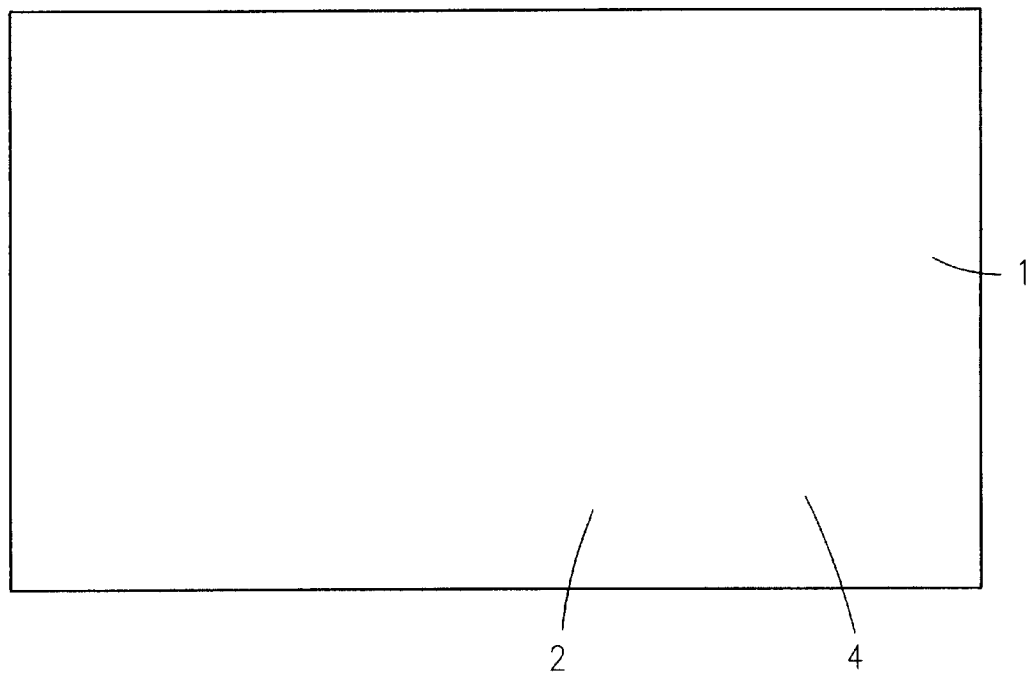
FIG. 4 illustrates the back side of an adhesive patch with a release liner attached to the patch.
Figure 5:
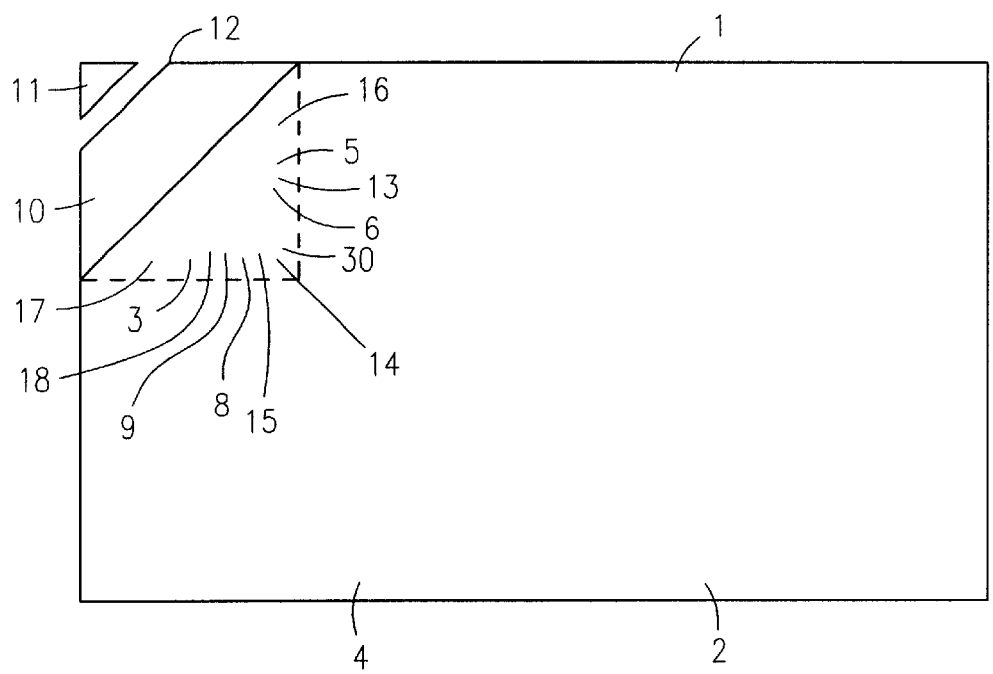
FIG. 5 illustrates the back side of an adhesive patch of the present invention with a release liner attached to the patch, wherein the patch is partially detached from the release liner.
Figure 6:
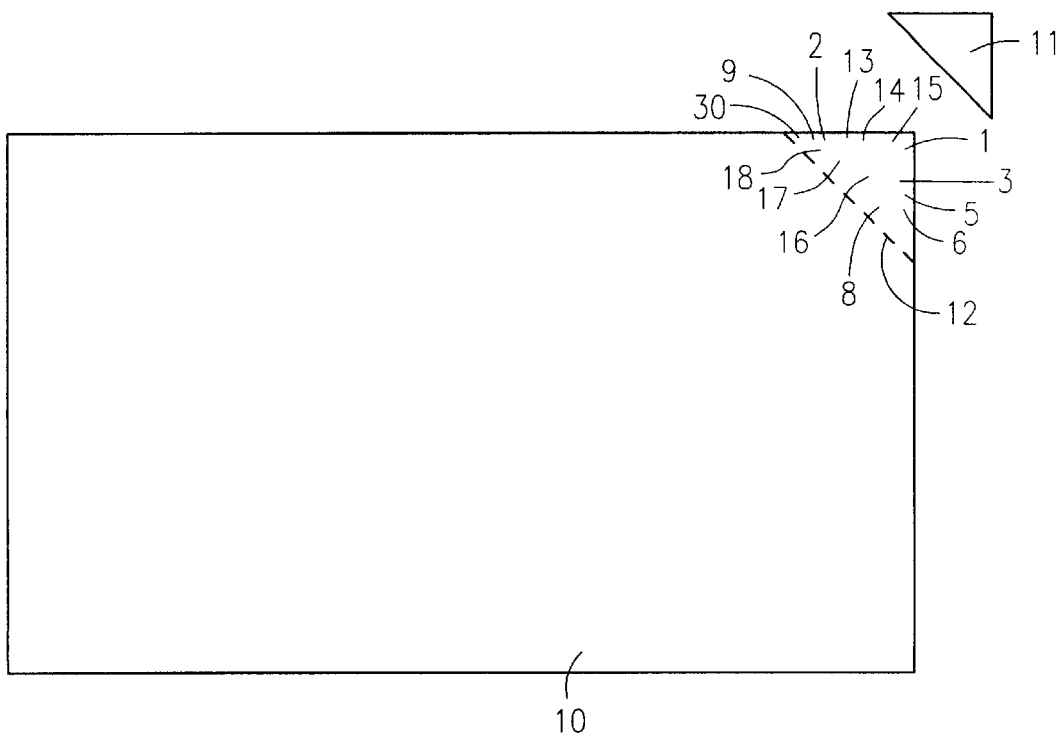
FIG. 6 illustrates the back side of an adhesive patch of the present invention with a release liner attached to the patch, wherein the patch is partially detached from the release liner.

The present invention provides a unique adhesive vehicle. The vehicle has pressure sensitive adhesive qualities due to its composition and viscoelastic nature. The adhesive is hydrophilic and therefore water can dissolve into or evaporate from the adhesive, depending on the conditions to which it is exposed. This water exchange capability implies that if the adhesive is on a suitably porous backing and is applied to the skin, it will not be occlusive as most drug delivery patches are. The occlusive nature of conventional drug delivery patches is thought to play an important role in enhancing drug absorption, but also often results in greater incidence of skin irritation. The relatively low occlusiveness of the present invention can be envisioned to be a special adhesive ointment or gel which is water-breathable, such as a water washable or water soluble ointment or gel.

The present invention provides an ointment or gel on a backing. The ointment or gel includes an effective, known, and safe amount of a medicament that is useful for treating acne; and a pressure sensitive adhesive. The backing is pliable and/or stretchable. Since the backing can be porous and/or vapor permeable, many consumers typically refer to the device as a "patch." As such, the device (i.e., the ointment or gel on the backing) will herein be referred to as a patch, as a skin patch, and/or as an acne patch. It is appreciated that those skilled in the art understand that the term patch is used to refer to the device and is not otherwise limiting in any manner.

The present invention provides a water insoluble, protective, adhesive patch useful for treating or preventing acne or a pimple. The patch prevents infections associated with acne or a pimple. The patch administers to the skin an effective and known amount of a topical acne drug. The patch maintains the adhesiveness of the adhesive and the stability of the topical acne drug over a prolonged period of time typically experienced in the manufacturing, packaging, shipping, and/or the storage of the patch. The topical acne drug, solvent, and pressure sensitive adhesive are positioned on and in at least a portion of the adhesive patch, such that they are partially embedded in at least a portion of the adhesive patch. Additionally, the patch complies with FDA regulations (e.g., 21 C.F.R. Chapter 1, Section 333, Subpart D- Topical Acne Drug Products, Apr. 1, 2000 Edition). The adhesive patch of the present invention can include a gel that is not water-based. The adhesive patch includes a backing that is treated with a hydrophobic sizing agent (e.g., a fluorocarbon solution, silicone, or a combination thereof). The use of such backing prevents immediate wick through and maintains the hydrogel from penetrating the backing too quickly. In addition, the use of such backing provides a patch with a higher yield improvement and superior holdout properties. The use of such backing also obviates the need for a backing liner or a release liner. In such an embodiment, the adhesive patch can exist as a self wound adhesive patch.

As used herein, "holdout" refers to the physical properties of a backing, relating to the ability of a specific class of gels or ointments to penetrate, cross-link, wet, and/or cure within the matrix of the backing. A specific class of gels or ointments may or may not be able to penetrate a given backing. Upon penetration of a gel or ointment into a backing, the gel or ointment will cross-link, wet, or cure in the backing. As such, the holdout properties are a degree of the ability of the gel or ointment to prevent the penetration, cross-linking, wetting, and/or curing within the matrix of the backing. Those backings with superior holdout properties will typically prevent, decrease, or lessen the likelihood of the ointment or gel from wetting the backing; will typically prevent, decrease, or lessen the likelihood of the ointment or gel from cross-linking within the matrix of the backing; will typically prevent, decrease, or lessen the likelihood of the ointment or gel from curing within the matrix of the backing; and/or will typically prevent, decrease, or lessen the likelihood of the ointment or gel from penetrating the matrix of the backing.

It has been surprisingly discovered that the use of a treated backing, such as a fluorocarbon treated non-woven backing, typically increases the yield of an adhesive patch. The use of a backing material that has been treated with a sizing agent allows for the effective control of the rate of penetration, such that the gel or ointment has solidified after it has begun to penetrate the backing, but before it has passed completely through the backing. In addition, the use of a backing material that has been treated with a sizing agent allows for the effective control of the depth to which the ointment or gel will easily penetrate before solidifying. It has been surprisingly discovered that increasing the control of the rate at which the ointment or gel penetrates the backing typically improves the overall yield of the production process by reducing the amount of material which must be discarded because the back side of the backing has become too tacky for either processing or for consumer acceptance.

Referring to FIGS. 1–10, an adhesive patch 1 of the present invention is provided. The adhesive patch 1 includes a therapeutic formulation 5 located on and in at least a portion of the front side 3 of the backing 2, such that the therapeutic formulation 5 is partially embedded in at least a portion of the front side 3 of the backing 2. The backing 2 is defined by a front side 3 (the side exposed to the skin during use) and a back side 4 (the side exposed to the environment during use). The backing 2 includes a flexible porous sheet of water insoluble material that provides support for the patch 1. The backing 2 should be nonirritating to human skin. The adhesive patch 1 can be vapor permeable. The backing 2 can also be porous, since porosity provides openings for receiving the therapeutic formulation 5 and it helps to assure that the patch 1 is vapor permeable. Specifically, the backing can retain the therapeutic formulation while allowing moisture from the skin to pass. The backing 2 can be woven or nonwoven. The backing can have any suitable thickness, provided the suitable thickness allows for a flexible, bendable, pliable, vapor permeable, and/or a stretchable sheet of water insoluble porous material. Specifically, the thickness of the backing can be about 0.001 mm to about 3.0 mm, or about 0.025 mm to about 1.25 mm.

The backing 2 is a self-supporting sheet of water insoluble, polymeric or natural material that provides strength and integrity for the therapeutic formulation 5. Preferably, the backing 2 includes nonwoven fabric.

At least a portion of the backing is treated with a hydrophobic sizing agent 8 such that the portion of the backing that is treated with the hydrophobic sizing agent 8 has a surface energy of about 20 dynes/cm$^2$ to about 65 dynes/cm$^2$. Specifically, the portion of the backing that is treated with the hydrophobic sizing agent 8 has a surface energy of about 27 dynes/cm$^2$ to about 56 dynes/cm$^2$. The hydrophobic sizing agent 8 lowers the surface energy of the portion of the backing that is treated with the hydrophobic sizing agent 8. Any suitable hydrophobic sizing agent 8 can be employed, provided the portion of the backing that is treated with the hydrophobic sizing agent 8 has a surface energy of about 20 dynes/cm$^2$ to about 65 dynes/cm$^2$. Suitable hydrophobic sizing agents 8 include, e.g., fluorocarbon solutions, silicones, and combinations thereof. Specifically, the backing can be a non-woven backing that is treated with a fluorocarbon. For example, the fluorocarbon treated backing can be, e.g., Vilmed M 1585 W/HY, Vilmed M1585H/HY, Vilmed M 1586 W/HY, Vilmed M1586 H/HY, Vilmed M1570, Vilmed M1573 F, Vilmed M1573 FH, Vilmed M1577 F, Vilmed M1578 F, or Vilmed M1578 FH; which are all commercially available from Freudenberg Faservliesstoffe KG (Weinham, Germany). Alternatively, the silicone treated backing can be a non-woven backing that is coated with one or more silicone-containing compounds, e.g., polydimethyl siloxanes, dialkylsiloxanes, dimethylsiloxo vinyl alkenes, dialkylsiloxo vinyl alkenes, dimethylsiloxo acrylates, dialkylsiloxo acrylates, vinyl terminated polydimethylsiloxane, and vinyl terminated polydialkylsiloxane.

At least a portion of the backing is treated with the hydrophobic sizing agent 8. The portion of the backing that is treated with the hydrophobic sizing agent 8 is that portion of the backing that can typically contain the therapeutic formulation 5. The entire surface of the front side 3 of the backing 2 can be treated with the hydrophobic sizing agent 8 or a portion of the surface of the front side 3 of the backing 2 can be treated with the hydrophobic sizing agent 8. Preferably, the entire front side 3 of the backing 2 can be treated with the hydrophobic sizing agent 8. In addition to the surface of the front side 3 of the backing 2 being treated with the hydrophobic sizing agent 8, the hydrophobic sizing agent 8 can penetrate at least a portion of the underlying surface (e.g., one-tenth to about nine-tenths the thickness, or about one-fourth to about nine-tenths the thickness) of the backing 2. Preferably, the hydrophobic sizing agent 8 can penetrate the entire underlying surface of the backing 2.

The backing 2 can be manufactured from any suitable material, provided the suitable material can form a flexible, bendable, pliable, and/or stretchable backing. Preferably, the backing can be manufactured from a sheet of water insoluble porous material. For example, the backing 2 can include water insoluble polymeric fibers, a porous film, or any other kind of matrix with spaces within the matrix. A specific backing 2 is a lightweight, porous, pliable strip composed of a nonwoven fabric of polymeric or natural fibers such as polyester, cotton or cellulose fibers bonded together with a sizing resin. Preferably, the backing 2 can include polyester, polyurethane, polyolefin, polyamide fibers, natural fibers, cotton fibers, polycellulose fibers, or any mixture thereof. Specifically, the backing can include polycellulose fibers, polyester fibers, polyurethane fibers, polyolefin fibers, polyamide fibers, cotton fibers, copolyester fibers, or a mixture thereof. Additional stable, water insoluble flexible sheet materials and methods for manufacturing the suitable backings are disclosed, e.g., in U.S. Pat. No. 4,675,009; U.S. Pat. No. 5,536,263; U.S. Pat. No. 4,696,854; U.S. Pat. No. 5,741,510, and references cited therein, and are suitable as backings according to the present invention. The infusion of the therapeutic formulation 5 into the backing 2 can be accomplished with the use of a continuous process mixer, as disclosed, e.g., in U.S. Pat. No. 5,536,263, and references cited therein.

Suitable fluorocarbon treated backings include, e.g., Vilmed M 1585 W/HY, Vilmed M1585H/HY, Vilmed M1586 W/HY, Vilmed M1586 H/HY, Vilmed M1570, Vilmed M1573 F, Vilmed M1573 FH, Vilmed M1577 F, Vilmed M1578 F, and Vilmed M1578 FH; which are all commercially available from Freudenberg Faservliesstoffe KG (Weinham, Germany).

Alternatively, the backing can be a non-woven backing that is treated by coating, either on the front side of the backing, the back side of the backing, or both the front and back sides of the backing, with a silicone-containing compound. Suitable silicone-containing compounds include, e.g., polydimethyl siloxanes, dialkylsiloxanes, dimethylsiloxo vinyl alkenes, dialkylsiloxo vinyl alkenes, dimethylsiloxo acrylates, dialkylsiloxo acrylates, vinyl terminated polydimethylsiloxane, and vinyl terminated polydialkylsiloxane. The silicone-containing compounds are commercially available from, e.g., Goldschmidt Chemical Corp. (Essen, Germany); GE Silicones (Waterford, N.Y.); Wacker Silicone Corp. (Adrian, Mich.); and Dow Corning Corp. (Midland, Mich.).

The backing can be manufactured from a suitable non-woven fabric that is commercially available from, e.g., Freudenberg Faservliesstoffe KG (Weinham, Germany); Sontara Technologies (division of DuPont Corporation) (Old Hickory, Tenn.); Lystil S. A. Brignoud Cedex, France); Dexter Nonwovens (Windsor Locks, Conn.); and Chicopee (New Brusnwick, N.J.). Other commercial vendors that supply suitable non-woven fabrics can be found at the Technical Textile website (http ://www.technical-textiles.net/technical-textiles-index/orgL.htm).

Figure 10:
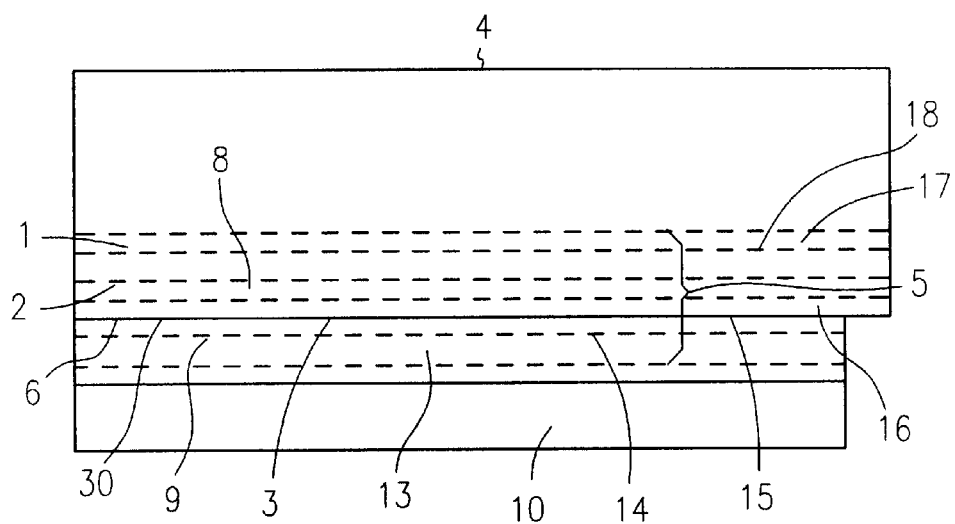
FIG. 10 illustrates an enlarged cross-sectional view of specific patch of the present invention.

As shown in FIGS. 1–6 and 10, the backing 2 includes a front side 3 and a back side 4. The patch 1 includes a therapeutic formulation 5 located on and in at least a portion of the front side 3 of the backing 2. As such, the therapeutic formulation 5 can be located on the entire surface of the front side 3 of the backing 2 or the therapeutic formulation 5 can be located on a portion of the surface of the front side 3 of the backing 2. Preferably, the therapeutic formulation 5 can be located on the entire front side 3 of the backing 2. In addition to being located on the surface of the front side 3 of the backing 2, the therapeutic formulation 5 can be located in at least a portion of the front side 3 of the backing 2 (i.e., the therapeutic formulation 5 can be partially embedded into the backing 2). As shown in FIG. 10, the therapeutic formulation 5 can penetrate a substantial portion of the front side 3 of the backing 2, as disclosed, e.g., in U.S. Pat. No. 5,536,263, and references cited therein. For example, the therapeutic formulation 5 can penetrate about one-tenth to about nine-tenths the thickness of the backing 2, or about one-fourth to about nine-tenths the thickness of the backing 2. As such, the therapeutic formulation 5 can be partially embedded into the backing 2. Preferably, the therapeutic formulation 5 can be located on the entire front side 3 of the backing 2 and partially in the front side 3 of the backing 2 (i.e., the therapeutic formulation 5 is partially embedded into the backing 2). Alternatively, a portion of the front side 3 of the backing 2 can include the therapeutic formulation 5 and other portions of the front side 3 of the backing 2 can include any combination of the adhesive 14, topical acne drug 15, and solvent 13. For example, a central circular portion of the front side 3 of the backing 2 can include the therapeutic formulation 5 while the remaining portions of the front side 3 of the backing 2 include only the adhesive 14. The therapeutic formulation 5, being partially embedded into the front side 3 of the backing 2, imparts strength and structure into the adhesive patch 1. For example, when the therapeutic formulation 5 is partially embedded into the backing 2, the likelihood that the adhesive patch 1 will tear apart when separated from the release liner 10 is minimized. When the adhesive skin patch 1 is placed upon the skin of a patient (e.g., human), the therapeutic formulation 5 can be in continuous contact with the skin surface of the patient.

Preferably, the patch 1, upon contact with skin, will allow the skin to breathe. More preferably, the patch 1, upon prolonged contact with skin, will hold in place the therapeutic formulation 5 and will permit the skin to breathe over prolonged periods of time typically experienced with the use of the patch, e.g., up to about 12 hours, up to about 8 hours, or up to about 6 hours.

As shown in FIGS. 3–6 and 10, the patch 1 can be reversibly attached to a release liner 10. The release liner 10 helps to maintain the adhesiveness of the patch 1 prior to use, such as during manufacturing, packaging, shipping, and/or storage. Any suitable release liner 10 can be employed for use in the present invention. Suitable release liners 10 are readily known to those of skill in the art. See, e.g., U.S. Pat. No. 4,675,009; U.S. Pat. No. 5,536,263; U.S. Pat. No. 4,696,854; U.S. Pat. No. 5,741,510, and references cited therein for further descriptions of release liners 10 useful in the present invention. The release liner 10 can include a perforation 12 that allows the tab section 11 of the release liner 10 to be removed (see, FIGS. 3, 5, and 6). Removal of the tab section 11 of the release liner 10 allows the patch 1 to be removed from the release liner 10 with relative ease.

As used herein, a "topical acne drug" is a compound or combination of compounds that effectively prevents and/or treats acne or a pimple. Any suitable topical acne drug 15 can be employed, provided the topical acne drug 15 effectively treats and/or prevents acne or a pimple and the topical acne drug 15 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1.

Suitable topical acne drugs are disclosed, e.g., in *Physician's Desk Reference* (*PDR*), Medical Economics Company (Montvale, N.J.), (53rd Ed.), 1999; *Mayo Medical Center Formulary, Unabridged Version*, Mayo Clinic (Rochester, Minn.), January 1998: *Merck Index*, An Encyclopedia of Chemicals, Drugs, and Biologicals, (11th Ed.), Merck & Co., Inc. (Rahway, N.J.), 1989; and references cited therein. Suitable topical acne drugs 15 include, e.g., salicylic acid, resorcinol, resorcinol acetate, benzoyl peroxide, sulfur, retinol, retinoic acid, citric acid, an alpha hydroxy acid, retinal, pharmaceutically acceptable salts thereof, and combinations thereof. Preferably, the topical acne drug 15 is salicylic acid, or a pharmaceutically acceptable salt thereof.

The topical acne drug 15 can be present in any appropriate and suitable amount, provided the amount of topical acne drug 15 is effective to treat and/or prevent acne or a pimple and the amount of topical acne drug 15 remains stable in the therapeutic formulation 5 over a prolonged period of time. Preferably, the stability is over a prolonged period of time, e.g., up to about 3 years, up to about 1 year, or up to about 6 months, typically experienced in the manufacturing, packaging, shipping, and/or storage of the patch 1. Typically, the topical acne drug 15 can be present in about 0.01 wt. % to about 99.9 wt. % of the therapeutic formulation 5. Specifically, the amount of topical acne drug present in the therapeutic formulation 5 can be up to about 5.0 wt. % of the therapeutic formulation 5, up to 4.0 wt. % of the therapeutic formulation 5, up to 3.0 wt. % of the therapeutic formulation 5, or in about 0.5 wt. % to about 2.0 wt. % of the therapeutic formulation 5. Preferably, the topical acne drug 15 and amount thereof will comply with FDA regulations (e.g., 21 C.F.R. Chapter 1, Section 333, Subpart D- Topical Acne Drug Products, Apr. 1, 2000 Edition).

The amount of topical acne drug 15 present in the therapeutic formulation 5 will typically depend upon the specific compound or compounds employed as the topical acne drug 15. For example, salicylic acid can be present up to about 99.9 wt. % of the therapeutic formulation 5, up to about 10.0 wt. % of the therapeutic formulation 5, up to 2.0 wt. % of the therapeutic formulation 5, or up to about 2.0 wt. % of the therapeutic formulation 5.

Specifically, resorcinol can be present up to about 2 wt. % of the therapeutic formulation 5, in accordance with 21 CFR Ch. 1, § § 333.320(a) and 333.310(a). Specifically, resorcinol monoacetate can be present up to about 3 wt. % of the therapeutic formulation 5, in accordance with 21 CFR Ch.1, §§ 333.320(b) 333.310(b). Specifically, salicylic acid can be present in about 0.5 wt. % to about 2.0 wt. % of the therapeutic formulation5, in accordance with 21 CFR Ch.1, § 333.310(c). Specifically, sulfur can be present in about 3.0 wt. % to about 10.0 wt. % of the therapeutic formulation 5, in accordance with 21 CFR Ch.1, § 333.310(d).

The topical acne drug 15 can preferably be located on and in any portion of the therapeutic formulation 5, which is located on the front side 3 of the backing 2. Preferably, the topical acne drug 15 can be located on and in the entire portion of the therapeutic formulation 5. When the adhesive skin patch 1 is placed upon the skin of a patient (e.g., human), the topical acne drug 15 can be in continuous contact with the skin surface of the patient.

The topical acne drug 15 can be located on the entire surface of the front side 3 of the backing 2 or the topical acne drug 15 can be located on a portion of the surface of the front side 3 of the backing 2. Preferably, the topical acne drug 15 can be located on the entire front side 3 of the backing 2. In addition to being located on the surface of the front side 3 of the backing 2, the topical acne drug 15 can be located in at least a portion of the front side 3 of the backing 2 (i.e., the topical acne drug 15 can be partially embedded into the backing 2). As shown in FIG. 10, the topical acne drug 15 can penetrate a substantial portion of the front side 3 of the backing 2, as disclosed, e.g., in U.S. Pat. No. 5,536,263, and references cited therein. For example, the topical acne drug 15 can penetrate about one-tenth to about nine-tenths the thickness of the backing 2, or about one-fourth to about nine-tenths the thickness of the backing 2. As such, the topical acne drug 15 can be partially embedded into the backing 2. When the adhesive skin patch 1 is placed upon the skin of a patient (e.g., human), the topical acne drug 15 can be in continuous contact with the skin surface of the patient.

As used herein, "acne" refers to an inflammatory follicular, papular, or pustular eruption involving the sebaceous apparatus. Acne is a disease of the skin where sebaceous glands are numerous (e.g., face, upper back, and chest) and characteristic lesions are present, e.g., open (blackhead) comedo, closed (whitehead) comedo, papule, pustule, or nodule. It is believed that acne results from the thickening of the follicular opening, increased sebum production, the presence of bacteria, or the host's inflammatory response. The types of acne include, e.g., acne conglobata, chloracne, and rosacea. See, e.g., *Stedman's Medical Dictionary*, 25th Ed., illustrated, Williams & Wilkins, Baltimore, Md., pp. 15–16 (1990) and *Mosby's Medical, Nursing, & Allied Health Dictionary*, (5th Ed.), Mosby: St. Louis, p.19 (1998).

As used herein, a "pimple" refers to a small papule, pustule, or furnacle. See, e.g., *Mosby's Medical, Nursing, & Allied Health Dictionary*, (5th Ed.), Mosby: St. Louis, p.1267 (1998).

The solvent 13 can act as a carrier for, and preferably can dissolve, the topical acne drug 15 and/or the adhesive 14. Any suitable solvent 13 can be employed, provided the solvent 13 effectively dissolves the topical acne drug 15 and/or the adhesive 14 and the solvent 13 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1.

The solvent 13 can include one or more organic compounds, one or more inorganic compounds, or mixtures thereof. Preferably, the solvent 13 will include one or more organic compounds, e.g., esters, terpenes, alcohols, ketones, aldehydes, fatty acids, partially or fully esterified fatty acids, wherein the structures are cyclic, non cylcic (e.g., alkyl), alicyclic (i.e., a bridged ring compound), or aromatic, as well as organic compounds having combinations of these functional groups. Suitable exemplary solvents 13 are disclosed, e.g., in Aldrich Handbook of Fine Chemicals, 2000–2001 (Milwaukee, Wis.).

Preferably, the solvent 13 includes a polyhydric alcohol (propylene glycol and/or ethylene glycol), water, or a combination thereof. The solvent 13 can be employed in any suitable amount, provided the amount of solvent 13 is effective to dissolve the topical acne drug 15 and/or the pressure sensitive adhesive 14 and the effective amount of solvent 13 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. Specifically, the solvent 13 can be present in about 6.0 wt. % to about 24.0 wt. % of the therapeutic formulation 5. Specifically, the solvent 13 can include propylene glycol in about 3.0 wt. % to about 11.0 wt. % of the therapeutic formulation 5. Specifically, the solvent 13 can include water in about 2.0 wt. % to about 20.0 wt. % of the therapeutic formulation 5.

The solvent 13 can preferably be located on and in any portion of the therapeutic formulation 5, which is located on the front side 3 of the backing 2. Preferably, the solvent 13 can be located on and in the entire portion of the therapeutic formulation 5. When the adhesive skin patch 1 is placed upon the skin of a patient (e.g., human), the solvent 13 can be in continuous contact with the skin surface of the patient.

The solvent 13 can be located on the entire surface of the front side 3 of the backing 2 or the solvent 13 can be located on a portion of the surface of the front side 3 of the backing 2. Preferably, the solvent 13 can be located on the entire front side 3 of the backing 2. In addition to being located on the surface of the front side 3 of the backing 2, the solvent 13 can be located in at least a portion of the front side 3 of the backing 2 (i.e., the solvent 13 can be partially embedded into the backing 2). As shown in FIG. 10, the solvent 13 can penetrate a substantial portion of the front side 3 of the backing 2, as disclosed, e.g., in U.S. Pat. No. 5,536,263, and references cited therein. For example, the solvent 13 can penetrate about one-tenth to about nine-tenths the thickness of the backing 2, or about one-fourth to about nine-tenths the thickness of the backing 2. As such, the solvent 13 can be partially embedded into the backing 2. When the adhesive skin patch 1 is placed upon the skin of a patient (e.g., human), the solvent 13 can be in continuous contact with the skin surface of the patient.

Any suitable pressure sensitive adhesive 14 can be employed, provided the pressure sensitive adhesive 14 provides the requisite adhesiveness to the patch 1 and the pressure sensitive adhesive 14 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. It is appreciated that the suitable pressure sensitive adhesives would be known to those skilled in the art. Suitable pressure sensitive adhesives are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably the pressure sensitive adhesive 14 is an acrylic ester copolymer.

Any suitable amount of pressure sensitive adhesive 14 can be employed, provided the amount of pressure sensitive adhesive 14 effectively provides the requisite adhesiveness to the patch 1 and the effective amount of the pressure sensitive adhesive 14 remains stable in the therapeutic formulation 5 over a prolonged period of time. Typically, the suitable amount of pressure sensitive adhesive 14 will depend upon the specific pressure sensitive adhesive 14 or pressure sensitive adhesives 14 employed. Typically, the therapeutic formulation 5 can include a pressure sensitive adhesive 14 in about 0.1 wt. % to about 50 wt. % of the therapeutic formulation 5. Preferably, the therapeutic formulation 5 can include a pressure sensitive adhesive 14 in about 0.5 wt. % to about 10.0 wt. % of the therapeutic formulation 5. More preferably, the therapeutic formulation 5 can include a pressure sensitive adhesive 14 in about 1.0 wt. % to about 15.0 wt. % of the therapeutic formulation 5. Specifically, the pressure sensitive adhesive 14 can include one or more acrylic ester copolymers, wherein all of the one or more acrylic ester copolymers are present, when combined, in about 3.0 wt. % to about 20.0 wt. % of the therapeutic formulation 5, or in about 5.0 wt. % to about 15.0 wt. % of the therapeutic formulation 5.

The pressure sensitive adhesive 14 can preferably be located on and in any portion of the therapeutic formulation 5, which is located on the front side 3 of the backing 2. Preferably, the pressure sensitive adhesive 14 can be located on and in the entire portion of the therapeutic formulation 5. When the adhesive skin patch 1 is placed upon the skin of a patient (e.g., human), the pressure sensitive adhesive 14 can be in continuous contact with the skin surface of the patient.

The pressure sensitive adhesive 14 can be located on the entire surface of the front side 3 of the backing 2 or the pressure sensitive adhesive 14 can be located on a portion of the surface of the front side 3 of the backing 2. Preferably, the pressure sensitive adhesive 14 can be located on the entire front side 3 of the backing 2. In addition to being located on the surface of the front side 3 of the backing 2, the pressure sensitive adhesive 14 can be located in at least a portion of the front side 3 of the backing 2 (i.e., the pressure sensitive adhesive 14 can be partially embedded into the backing 2). As shown in FIG. 10, the pressure sensitive adhesive 14 can penetrate a substantial portion of the front side 3 of the backing 2, as disclosed, e.g., in U.S. Pat. No. 5,536,263, and references cited therein. For example, the pressure sensitive adhesive 14 can penetrate about one-tenth to about nine-tenths the thickness of the backing 2, or about one-fourth to about nine-tenths the thickness of the backing 2. As such, the pressure sensitive adhesive 14 can be partially embedded into the backing 2. When the adhesive skin patch 1 is placed upon the skin of a patient (e.g., human), the pressure sensitive adhesive 14 can be in continuous contact with the skin surface of the patient.

The pressure sensitive adhesive 14 can optionally include one or more polymers 9. The polymer 9 provides structure and strength to the pressure sensitive adhesive 14 or to the therapeutic formulation 5. Any suitable polymer 9 can be employed, provided the polymer 9 provides structure and strength to the pressure sensitive adhesive 14 or to the therapeutic formulation 5, and the polymer 9 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. Suitable polymers 9 include, e.g., karaya, a polyacrylamide, xanthum gum, guar gum, a natural polymer, a synthetic polymer, a hydrophilic polymer, a hydrocolloidal polymer, starch, a starch derivative, vinyl acetate copolymer, polyvinyl pyrrolidone, polyethylene oxide, algin, derivatives of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS or a mixture thereof. Other suitable polymers 9 are disclosed, e.g., in U.S. Pat. No. 4,675,009; U.S. Pat. No. 5,536,263; U.S. Pat. No. 4,696,854; U.S. Pat. No. 5,741,510, and references cited therein. Preferably, the polymer 9 is polyacrylamide, karaya, or a combination thereof.

Any suitable amount of polymer 9 can be employed, provided the amount of polymer 9 effectively provides structure and strength to the pressure sensitive adhesive 14 or to the therapeutic formulation 5, and the effective amount of polymer 9 remains stable in the therapeutic formulation 5 over a prolonged period of time. Preferably, the stability is over a prolonged period of time, e.g., up to about 3 years, up to about 1 year, or up to about 6 months, typically experienced in the manufacturing, packaging, shipping, and/or storage of the patch 1. Typically, the suitable amount of polymer 9 will depend upon the specific polymer 9 or polymers 9 employed. Specifically, karaya can be employed as the polymer 9 in about 5.0 wt. % to about 35 wt. % of the therapeutic formulation 5, or in about 8.0 wt. % to about 25 wt. % of the therapeutic formulation 5. Specifically, polyacrylamide can be employed as the polymer 9 in about 5.0 wt. % to about 35 wt. % of the therapeutic formulation 5, or in about 8.0 wt. % to about 25 wt. % of the therapeutic formulation 5.

The therapeutic formulation 5 can optionally include one or more fillers 6. Any suitable filler 6 can be employed. Suitable fillers 6 include malto dextrin, dextrin, 70% sorbitol water, modified starches, depolymerized starches, and methylcellulose. As used herein, "malto dextrin" is a dextrose equivalent, wherein dextrose is D-glucose. Malto dextrin is commercially available as Amaizo Lodex 5 from American Maize-Products (Hammond, Ind.). Any suitable amount of filler can be employed in the therapeutic formulation 5. The suitable amount of filler can depend in part upon the specific filler or fillers present in the therapeutic formulation 5. For example, malto dextrin can be present up to about 20.0 wt.

% of the therapeutic formulation 5, or can be present in about 1.0 wt. % to about 10.0 wt. % of the therapeutic formulation 5.

Alternatively, the adhesive 14 can include a hot melt pressure sensitive adhesive or solvent based pressure sensitive adhesive (e.g., polyacrylate, polyisobutylene, and polybutene), rubber, silicone based pressure sensitive adhesives (e.g., polydimethylsiloxane and resin mixtures), polystyrene-polybutadiene-polystyrene, polystyrene-polyisoprene-polystyrene, polystyrene-poly(ethylene-butylene)-polystyrene block polymers, or any combination thereof. In addition, the adhesive 14 can include a resin emulsion adhesive, wherein the resin emulsion adhesive can include vinyl acetate resin, acrylic ester copolymer, vinyl actetate/diocyl maleate copolymer, acrylic copolymer, or any combination thereof.

Other suitable adhesives 14 are disclosed, e.g., in U.S. Pat. No. 4,675,009; U.S. Pat. No. 5,536,263; U.S. Pat. No. 4,696,854; U.S. Pat. No. 5,741,510, and references cited therein.

The therapeutic formulation 5 can optionally include one or more suitable antibiotic agents 16. As used herein, an "antibiotic agent" is any compound having activity against either Gram-positive or Gram-negative organisms (i.e., inhibits the growth or destroys the development of either Gram-positive or Gram-negative organisms). *Stedman's Medical Dictionary Illustrated*, (25th Ed.), Williams & Wilkins: Baltimore (1990) and *Mosby's Medical. Nursing, & Allied Health Dictionary*, (5th Ed.), Mosby: St. Louis (1998).

Any suitable antibiotic agent 16 can be employed, provided the antibiotic agent 16 effectively inhibits the growth or destroys the development of either Gram-positive or Gram-negative organisms and the antibiotic agent 16 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. Suitable antibiotic agents 16 are disclosed, e.g., in *Physician's Desk Reference (PDR)*, Medical Economics Company (Montvale, N.J.), (53rd Ed.), 1999: *Mayo Medical Center Formulary, Unabridged Version*, Mayo Clinic (Rochester, Minn.), January 1998: *Merck Index*, An Encyclopedia of Chemicals, Drugs, and *Biologicals*, (11th Ed.), Merck & Co., Inc. (Rahway, N.J.), 1989; *University of Wisconsin Antimicrobial Use Guide*, http://www.medsch.wisc.edu/clinsci/ amcg/ amcg.html; *Introduction on the Use of the Antibiotics Guideline, Descriptions of Specific Antibiotic Classes*, Thomas Jefferson University, http://jeffline.tju.edu/CWIS/OAC/ antibiotics_guide/intro.html; and references cited therein.

Suitable classes of antibiotic agents 16 include, e.g., β-lactams, aminoglycosides, antifungal agents, and combinations thereof. Suitable antibiotic agents 16 include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenam, meropenem, cilistatin, cefadroxil, cefazolin, cephalexin, cephalothin, cefaclor, cefamandole, cefonicid, cefoxitin, cefuroxine, cefoperazone, cefotaxime, ceftazidime, ceftazidime, ceftizoxime, ceftriaxone, moxalactam, cefepine, bacitracin, vancomycin, aztreonam, amoxicillin, clavulanic acid, benzathine, penicillin g, penicillin v, ampicillin, carbenicillin indamyl, carbenicillin, mezlocillin, piperacillin, ticarcillin, cloxacillin, dicloxacillin, floxacillin, methicillin, nafcillin, oxacillin, colistmethate, polymixin b, trimethoprim, co-trimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythrmoycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, ascariasis, pinworm, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, foscamet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, pharmaceutically acceptable salts thereof, and combinations thereof. Specifically, the antibiotic agent can be erythromycin, tetracycline, clindamycin, cephalosporin, pharmaceutically acceptable salts thereof, or a combination thereof.

Any suitable amount of antibiotic agent 16 can be employed, provided the amount of antibiotic agent 16 employed effectively inhibits the growth or destroys the development of either Gram-positive or Gram-negative organisms and the effective amount of the antibiotic agent 16 remains stable in the therapeutic formulation 5 over a prolonged period of time. Preferably, the stability is over a prolonged period of time, e.g., up to about 3 years, up to about 1 year, or up to about 6 months, typically experienced in the manufacturing, packaging, shipping, and/or storage of the patch 1. Typically, the amount of antibiotic agent 16 will depend upon the specific antibiotic agent 16 or agents employed. Typically, the antibiotic agent 16 can be present up to about 99.9 wt. % of the therapeutic formulation 5, up to about 50 wt. % of the therapeutic formulation 5, up to about 25 wt. % of the therapeutic formulation 5, or up to about 10 wt. % of the therapeutic formulation 5. Preferably, the antibiotic agent 16 can be present up to about 5.0 wt. % of the therapeutic formulation 5, up to about 1.0 wt. % of the therapeutic formulation 5, or up to about 0.5 wt. % of the therapeutic formulation 5.

The antibiotic agent 16 can be located on the entire surface of the front side 3 of the backing 2 or the antibiotic agent 16 can be located on a portion of the surface ofthe front side 3 of the backing 2. Preferably, the antibiotic agent 16 can be located on the entire front side 3 of the backing 2. In addition to being located on the surface of the front side 3 of the backing 2, the antibiotic agent 16 can be located in at least a portion of the front side 3 of the backing 2 (i.e., the antibiotic agent 16 can be partially embedded into the backing 2). As shown in FIG. 10, the antibiotic agent 16 can penetrate a substantial portion of the front side 3 of the backing 2, as disclosed, e.g., in U.S. Pat. No. 5,536,263, and references cited therein. For example, the antibiotic agent 16 can penetrate about one-tenth to about nine-tenths the thickness of the backing 2, or about one-fourth to about nine-tenths the thickness of the backing 2. As such, the antibiotic agent 16 can be partially embedded into the backing 2. When the adhesive skin patch 1 is placed upon the skin of a patient (e.g., human), the antibiotic agent 16 can be in continuous contact with the skin surface of the patient.

The therapeutic formulation 5 can optionally include one or more humectants 17 to provide a moistening effect to the adhesive 14. For example, the humectant 17 can hydrate the polymer 9. Any suitable humectant 17 can be employed, provided the humectant 17 effectively provides a moistening effect to the adhesive 14 and the humectant 17 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. One suitable humectant 17 is glycerin. Other suitable humectants 17 s include polyhydric alcohols such as ethylene glycol, propylene glycol, triethylene glycol, tetraethylene glycol, and sorbitol.

Any suitable amount of humectant 17 can be employed, provided the amount of humectant 17 effectively provides a moistening effect to the adhesive 14 and the effective amount of humectant 17 remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. Typically, the suitable amount of humectant 17 will depend upon the specific humectant 17 or humectants 17 employed and the specific polymer 9 employed. For example, karaya, polyacrylamide, or a combination thereof can be employed as the polymer 9 and glycerin can be employed as the humectant 17 in about 20 wt. % to about 70 wt. % of the therapeutic formulation 5, in about 30 wt. % to about 60 wt. % of the therapeutic formulation 5, or in about 40 wt. % to about 50 wt. % of the therapeutic formulation 5.

The therapeutic formulation 5 can optionally include a compound that emulsifies the therapeutic formulation 5. One suitable compound that effectively emulsifies the therapeutic formulation 5 is pectin. The emulsifier (e.g., pectin) can be present in any suitable amount, provided the suitable amount is effective to emulsify the therapeutic formulation 5. Specifically, the emulsifier (e.g., pectin) can be present in about 1.0 wt. % to about 20.0 wt. % of the therapeutic formulation 5, or in about 2.0 wt. % to about 10.0 wt. % of the therapeutic formulation 5.

The therapeutic formulation 5 can optionally include an antiseptic 30. As used herein, an "antiseptic" is an agent or substance capable of effecting antisepsis, i.e., the prevention of infection by inhibiting the growth of infectious agents. *Stedman's Medical Dictionary*, 25th Ed., illustrated, Williams & Wilkins, Baltimore, Md., p. 100 (1990). Any suitable antiseptic 30 can be employed, provided the suitable antiseptic 30 effectively inhibits the growth of infectious agents. Suitable antiseptics 30 include, e.g., triclosan, phenoxy isopropanol, chlorhexidine gluconate, povidone iodine, and any combination thereof. The antiseptic 30 can be employed in any suitable amount, provided the suitable mount of antiseptic 30 effectively inhibits the growth of infectious agents. For example, the antiseptic 30 can be employed up to about 20 wt. % of the of the therapeutic formulation 5, or up to about 10 wt. % of the of the therapeutic formulation 5.

The antiseptic 30 can be located on the entire surface of the front side 3 of the backing 2 or the antiseptic 30 can be located on a portion of the surface of the front side 3 of the backing 2. Preferably, the antiseptic 30 can be located on the entire front side 3 of the backing 2. In addition to being located on the surface of the front side 3 of the backing 2, the antiseptic 30 can be located in at least a portion of the front side 3 of the backing 2 (i.e., the antiseptic 30 can be partially embedded into the backing 2). As shown in FIG. 10, the antiseptic 30 can penetrate a substantial portion of the front side 3 of the backing 2, as disclosed, e.g., in U.S. Pat. No. 5,536,263, and references cited therein. For example, the antiseptic 30 can penetrate about one-tenth to about nine-tenths the thickness of the backing 2, or about one-fourth to about nine-tenths the thickness of the backing 2. As such, the antiseptic 30 can be partially embedded into the backing 2. When the adhesive skin patch 1 is placed upon the skin of a patient (e.g., human), the antiseptic 30 can be in continuous contact with the skin surface of the patient.

The therapeutic formulation 5 can optionally include a topical moisturizer 18 (i.e., skin protectant). Any suitable topical moisturizer 18 can be employed, provided the skin is effectively protected or moisturized and the skin protectant remains stable in the therapeutic formulation 5. Preferably, the stability is over a prolonged period of time, e.g., up to about 3 years, up to about 1 year, or up to about 6 months, typically experienced in the manufacturing, packaging, shipping, and/or storage of the patch 1. Suitable topical moisturizers 18 include, e.g. calamine, aloe, lanolin, glycerin, Vitamin E, Vitamin E acetate, farnesol, glycyrrhetinic acid, or any combination thereof. Specifically, the suitable topical moisturizer 18 can include, e.g., calamine, aloe, lanolin, glycerin, Vitamin E, Vitamin E acetate, farnesol, glycyrrhetinic acid, or any combination thereof. Additional suitable topical moisturizers 18 or skin conditioners are disclosed, e.g., in U.S. Pat. Nos. 6,096,334; 6,096,033; 5,741,510; 5,536,263; 4,675,009; 4,307,717; 4,274,420; 5,976,565; and 5,536,263.

As used herein, "calamine" is a pink powder of zinc oxide and a skin protectant containing about 98% zinc oxide and about 0.5% ferric oxide; "aloe" is the dried latex of leaves of Curaco Aloe (*Aloe barbadenis* Miller, *Aloe vera* Linne) or Cape Aloe (*Aloe ferox* Miller and hybrids), of the family Liliacaea. Aloe is commercially available as Aloe Vera Gel from Terry Laboratories (Melbourne, Fla.). Aloe Vera Gel is commercially available as Aloe Vera Gel 40X (20.0 wt. % solution in water), Aloe Vera Gel 1X (0.5 wt. % solution in water), Aloe Vera Gel 10X (5.0 wt. % solution in water), or solid Aloe Vera. The solid Aloe Vera can be dissolved in a carrier, such as water, to the desired concentration. In addition, the commercially available forms of Aloe Vera are optionally available as decolorized Aloe Vera.

As used herein, "Vitamin E" is 3,4-dihydro-2,5,7,8-tetramethyl-2-(4,8,12-trimethyltridecyl)-2H-1-benzopyran-6-ol; "Vitamin E acetate" is 3,4-dihydro-2,5,7,8-tetramethyl-2-(4,8,12-trimethyltridecyl)-2H-1 -benzopyran-6-ol acetate; "lanolin" is the fat-like secretion of the sebaceous glands of sheep (i.e., complex mixture of esters and polyesters of 33 high molecular weight alcohols and 36 fatty acids) which is deposited onto the wool fibers; "farnesol" is 3,7,11-trimethyl-2,6,10-dodecatrien-1-ol. Famesol is commercially available from American Radiolabeled Chemicals (ARC) (St. Louis, Mo.), and "glycyrrhetinic acid" is a pentacyclic triterpenoid derivative of the beta-amyrin type and is shown below:

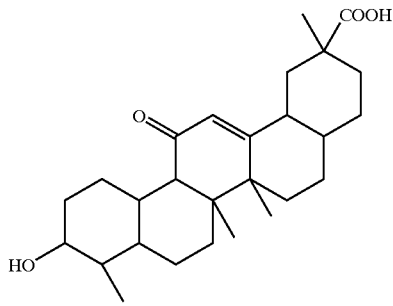

Any suitable amount of topical moisturizer 18 can be employed, provided the suitable amount of topical moisturizer 18 (i.e., skin protectant) effectively protects or moisturizes the skin and the effective amount of topical moisturizer 18 remains stable in the therapeutic formulation 5 over a prolonged period of time. The suitable and effective amount of topical moisturizer 18 will depend in part upon the specific topical moisturizer 18 present in the therapeutic formulation 5. For example, Aloe Vera Gel, 10X can be present up to about 40.0 wt. % of the therapeutic formulation 5. Preferably, Aloe Vera Gel, 10X can be present up to about 5.0 wt. % of the therapeutic formulation 5. More preferably, Aloe Vera Gel, 10X can be present up to about 1.0 wt. % of the therapeutic formulation 5. In addition, Vitamin E acetate can be present up to about 5 wt. % of the therapeutic formulation 5. Preferably, Vitamin E acetate can be present up to about 1.0 wt. % of the therapeutic formulation 5. More preferably, Vitamin E acetate can be present up to about 0.5 wt. % of the therapeutic formulation 5.

The topical moisturizer 18 can be located on the entire surface of the front side 3 of the backing 2 or the topical moisturizer 18 can be located on a portion of the surface of the front side 3 of the backing 2. Preferably, the topical moisturizer 18 can be located on the entire front side 3 of the backing 2. In addition to being located on the surface of the front side 3 of the backing 2, the topical moisturizer 18 can be located in at least a portion of the front side 3 of the backing 2 (i.e., the topical moisturizer 18 can be partially embedded into the backing 2). As shown in FIG. 10, the topical moisturizer 18 can penetrate a substantial portion of the front side 3 of the backing 2, as disclosed, e.g., in U.S. Pat. No. 5,536,263, and references cited therein. For example, the topical moisturizer 18 can penetrate about one-tenth to about nine-tenths the thickness of the backing 2, or about one-fourth to about nine-tenths the thickness of the backing 2. As such, the topical moisturizer 18 can be partially embedded into the backing 2. When the adhesive skin patch 1 is placed upon the skin of a patient (e.g., human), the topical moisturizer 18 can be in continuous contact with the skin surface of the patient.

The therapeutic formulation 5 can optionally include deionized water (DI). Any suitable amount of deionized water can be employed, provided the amount of deionized water maintains the adhesiveness of the adhesive 14 and maintains the appropriate stability of the therapeutic formulation 5. For example, deionized water can be present up to about 50 wt. % of the therapeutic formulation 5, up to about 40.0 wt. % of the therapeutic formulation 5, or up to about 30.0 wt. % of the therapeutic formulation 5. Preferably, deionized water can be present up to about 20.0 wt. % of the therapeutic formulation 5. More preferably, deionized water can be present up to about 10.0 wt. % of the therapeutic formulation 5.

The therapeutic formulation 5 can preferably remain stable over the period of time typically experienced with the manufacturing, packaging, shipping, and/or storage of the adhesive skin patch 1, e.g., up to about a month, up to about a year, or up to about two years. The stability of the topical acne drug 15, for example, is due in part to the therapeutic formulation 5 including the topical acne drug 15 in an adhesive formulation. The adhesive formulation is preferably a hydrogel that holds the topical acne drug 15 in an available form while maintaining the necessary stability, pressure sensitive adhesion and effectiveness over prolonged periods of time.

Figure 9:
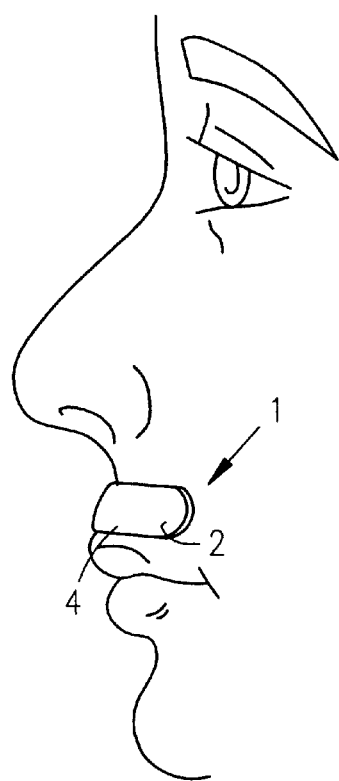
FIG. 9 illustrates a specific patch of the present invention in use.

As shown in FIG. 9, the adhesive skin patch 1 can be applied to the skin surface of a patient. The adhesive skin patch 1 can be applied to any suitable skin surface of the patient. Suitable skin surfaces in which the patch can be applied include, e.g., the face, neck, shoulder, chest, and back. Preferably, the adhesive skin patch 1 can be applied to the face of the patient (as shown in FIG. 9).

The adhesive patch also serves to effectively exfoliate the skin surface of a mammal (e.g., human). As used herein, "exfoliate" refers to the removal or detachment of superficial cells of an epithelium surface or horny layer (the stratum corneum) of the epidermis. Preferably, the skin cells, upon removal, are dead and are from the outermost one or two layers of the stratum corneum. The therapeutic formulation 5 possesses suitable physical properties (e.g., sufficient adhesiveness) to effectively remove or detach superficial cells of the epithelium surface or stratum corneum of the epidermis. The adhesive patch can be applied to the skin surface to be exfoliated for an effective period of time, e.g., from about one second to about twelve hours. After such effective period of time, the adhesive patch can be removed from the skin surface. Such exfoliation of the skin is believed to assist in the treatment and/or prevention of acne and/or pimples.

The patch serves as a protective covering or barrier. Such protection serves to prevent or diminish the likelihood that foreign objects (e.g., a person's finger, hair, clothing, etc.) will come into contact with the acne or pimple. This may effectively decrease the healing time of the acne or pimple.

The patch also serves to aesthetically cover skin blemishes such as acne and/or pimples. Since the public perception of acne and pimples is that they are unsightly, many individuals are self conscious and attempt to cover the skin blemishes with products that can further irritate the blemishes, thereby increasing the healing time. Many of these products do not effectively cover the entire skin blemishes for prolonged periods of time (e.g., up to about 8 hours, up to about 6 hours, or up to about 4 hours). The patch allows these individuals to completely cover the acne or pimples, thereby concealing the unsightly blemishes, while effectively treating the acne and/or pimples. As such, the patch can serve to aesthetically cover skin blemishes such as acne and/or pimples entirely for prolonged periods of time (e.g., up to about 8 hours, up to about 6 hours, or up to about 4 hours).

The adhesive skin patch 1 can have any suitable size and shape. In addition, the adhesive skin patch 1 can be cut, as desired, to provide an adhesive skin patch 1 of a suitable size and shape. The adhesive skin patch 1 can be cut with any suitable cutting device such as a scissors, scalpel, or knife.

Typically, the adhesive skin patch 1 will have a length of about 0.1 inch to about 8 inches, of about 0.20 inch to about 4 inches, or about 0.2 inches to about 2.0 inches. Preferably, the adhesive skin patch 1 can have a length of about 0.2 inches to about 0.7 inches.

Typically, the adhesive skin patch 1 will have a width of about 0.1 inch to about 4 inches, of about 0.20 inches to about 2.0 inches, or about 0.2 inches to about 1.0 inch. Preferably, the adhesive skin patch 1 can have a width of about 0.20 inch to about 0.75 inch.

Typically, the adhesive skin patch 1 will have a thickness of about 0.10 mm to about 1.0 mm, or about 0.20 mm to about 2.0 inches, or about 0.75 mm.

Figure 7:
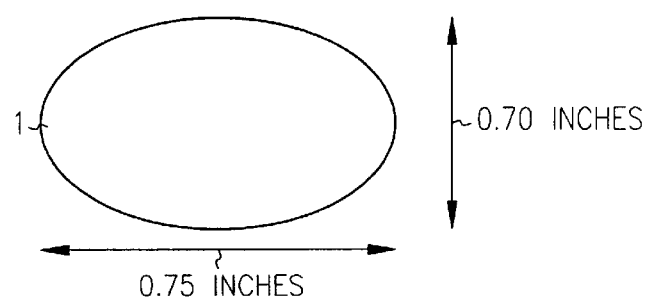
FIG. 7 illustrates a top view of a specific patch of the present invention.
Figure 8:
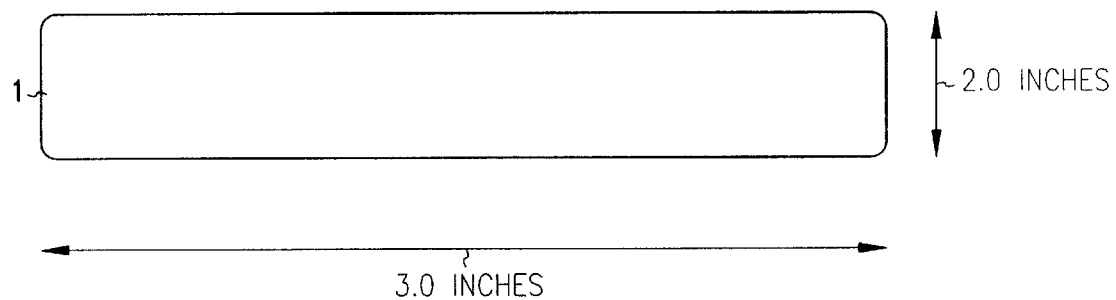
FIG. 8 illustrates a top view of a specific patch of the present invention.

In one specific embodiment of the present invention, the adhesive skin patch 1 can be oval or circular in shape (see, FIG. 7). The oval or circular patch 1 can have a diameter of about 0.1 inch to about 1.0 inches. Preferably, the oval or circular patch 1 can have a diameter of about 0.25 inch to about 1.0 inch. See, FIG. 7.

Preferably, as shown in FIGS. 3–6 and 10, the patch 1 can be reversibly attached to a release liner 10. Preferably, the release liner 10 can include more than one patch 1. More preferably, the release liner 10 can include about 2 to about 20 patches 1. The cost of having two or more patches 1 on a single release liner 10 is typically less expensive than skin patches 1 that are separately mounted on a single release liner 10. In addition, some consumers may prefer the ease and comfort of carrying a single patch assembly that includes a single release liner 10 and more than one (e.g., about 2 to about 20, or about 2 to about 10) adhesive patches 1 mounted on the single release liner 10.

The invention will now be illustrated by the following non-limiting Examples.

EXAMPLE 1

Specific Therapeutic Formulation

| Component | Weight % |
| --- | --- |
| Polyacrylamide | 12.0 |
| Malto Dextrin | 7.0 |
| Pectin | 4.0 |
| Glycerin | 47.4 |
| Propylene Glycol | 6.6 |
| Water | 5.6 |
| Adhesive | 13.0 |
| Salicylic Acid | 2.0 |
| Skin Conditioners | 2.4 |

EXAMPLE 2

Specific Therapeutic Formulation

| Component | Weight % |
| --- | --- |
| Polyacrylamide | 4.0 |
| Karaya | 9.0 |
| Malto Dextrin | 7.0 |
| Pectin | 4.0 |
| Glycerin | 49.6 |
| Propylene Glycol | 5.4 |
| Water | 6.2 |
| Adhesive | 10.0 |
| Salicylic Acid | 2.0 |
| Skin Conditioners | 2.8 |

EXAMPLE 3

Specific Therapeutic Formulation

| Component | Weight % |
| --- | --- |
| Karaya | 11.0 |
| Malto Dextrin | 8.0 |
| Pectin | 5.0 |
| Glycerin | 50.0 |
| Propylene Glycol | 6.4 |
| Water | 5.6 |
| Adhesive | 9.5 |
| Salicylic Acid | 2.0 |
| Skin Conditioners | 2.5 |

EXAMPLE 4

Specific Therapeutic Formulation

| Component | Weight % |
| --- | --- |
| polyacrylamide | 18.0 |
| Malto Dextrin | 8.0 |
| Pectin | 6.0 |
| Glycerin | 40.0 |
| Propylene Glycol | 5.4 |
| Water | 4.6 |
| Adhesive | 14.0 |
| Salicylic Acid | 2.0 |
| Skin Conditioners | 2.0 |

EXAMPLE 5

Specific Therapeutic Formulation

| Component | Weight % |
| --- | --- |
| Polyacrylamide | 16.0 |
| Malto Dextrin | 5.0 |
| Pectin | 4.0 |
| Glycerin | 49.8 |
| Propylene Glycol | 6.6 |
| Water | 6.0 |
| Adhesive | 10.0 |
| Salicylic Acid | 2.0 |
| Skin Conditioners | 0.6 |

EXAMPLE 6

Specific Therapeutic Formulation

| Component | Weight % |
| --- | --- |
| Karaya | 18.0 |
| Malto Dextrin | 5.0 |
| Pectin | 3.0 |
| Glycerin | 41.0 |
| Propylene Glycol | 8.4 |
| Water | 7.6 |
| Adhesive | 13.0 |
| Salicylic Acid | 2.0 |
| Skin Conditioners | 2.0 |

EXAMPLE 7

Specific Therapeutic Formulation

| Component | Weight % |
|---|---|
| Polyacrylamide | 13.0 |
| Malto Dextrin | 5.0 |
| Pectin | 4.0 |
| Glycerin | 49.6 |
| Propylene Glycol | 9.6 |
| Water | 8.0 |
| Adhesive | 7.0 |
| Salicylic Acid | 2.0 |
| Skin Conditioners | 1.8 |

EXAMPLE 8

Specific Therapeutic Formulation

| Component | Weight % |
|---|---|
| Polyacrylamide | 8.0 |
| Malto Dextrin | 7.0 |
| Pectin | 6.0 |
| Glycerin | 51.8 |
| Propylene Glycol | 8.6 |
| Water | 6.0 |
| Adhesive | 10.0 |
| Salicylic Acid | 2.0 |
| Skin Conditioners | 0.6 |

EXAMPLE 9

Specific Therapeutic Formulation

| Component | Weight % |
|---|---|
| Polyacrylamide | 25.0 |
| Malto Dextrin | 2.0 |
| Pectin | 2.0 |
| Glycerin | 45.0 |
| Propylene Glycol | 8.4 |
| Water | 4.6 |
| Adhesive | 9.0 |
| Salicylic Acid | 2.0 |
| Skin Conditioners | 2.0 |

EXAMPLE 10

Specific Therapeutic Formulation

| Component | Weight % |
|---|---|
| Polyacrylamide | 17.0 |
| Malto Dextrin | 6.0 |
| Pectin | 6.0 |
| Glycerin | 46.6 |
| Propylene Glycol | 9.6 |
| Water | 4.0 |
| Adhesive | 2.0 |
| Salicylic Acid | 2.0 |
| Skin Conditioners | 6.8 |

EXAMPLE 11

Specific Therapeutic Formulation

| Component | Weight % |
|---|---|
| Polyacrylamide | 16.0 |
| Malto Dextrin | 5.0 |
| Pectin | 4.0 |
| Glycerin | 49.0 |
| Propylene Glycol | 6.6 |
| Water | 5.6 |
| Adhesive | 10.0 |
| Salicylic Acid | 2.0 |
| Skin Conditioners | 1.8 |

EXAMPLE 12

Specific Therapeutic Formulation

| Component | Weight % |
|---|---|
| Polyacrylamide | 10.0 |
| Malto Dextrin | 3.4 |
| Pectin | 2.0 |
| Glycerin | 45.0 |
| Propylene Glycol | 4.6 |
| Water | 18.0 |
| Adhesive | 13.0 |
| Salicylic Acid | 2.0 |
| Skin Conditioners | 2.0 |

EXAMPLE 13

Specific Therapeutic Formulation

| Component | Weight % |
|---|---|
| Karaya | 24.0 |
| Malto Dextrin | 5.0 |
| Pectin | 3.0 |
| Glycerin | 42.0 |
| Propylene Glycol | 5.4 |
| Water | 5.6 |
| Adhesive | 9.0 |
| Salicylic Acid | 2.0 |
| Skin Conditioners | 4.0 |

EXAMPLE 14

Specific Therapeutic Formulation

| Component | Weight % |
|---|---|
| Polyacrylamide | 13.0 |
| Karaya | 16.0 |
| Malto Dextrin | 2.0 |
| Pectin | 3.0 |
| Glycerin | 44.6 |
| Propylene Glycol | 5.4 |
| Water | 5.2 |
| Adhesive | 5.0 |
| Salicylic Acid | 2.0 |
| Skin Conditioners | 3.8 |

EXAMPLE 15

Specific Therapeutic Formulation

| Component | Weight % |
|---|---|
| Polyacrylamide | 12.0 |
| Malto Dextrin | 7.5 |
| Pectin | 4.0 |
| Glycerin | 48.4 |
| Propylene Glycol | 6.9 |
| Water | 5.6 |
| Adhesive | 13.0 |
| Salicylic Acid | 0.2 |
| Skin Conditioners | 2.4 |

EXAMPLE 16

Specific Therapeutic Formulation

| Component | Weight % |
|---|---|
| Polyacrylamide | 16.0 |
| Malto Dextrin | 6.5 |
| Pectin | 4.0 |
| Glycerin | 49.8 |
| Propylene Glycol | 6.6 |
| Water | 6.0 |
| Adhesive | 10.0 |
| Salicylic Acid | 0.5 |
| Skin Conditioners | 0.6 |

EXAMPLE 17

Specific Therapeutic Formulation

| Component | Weight % |
|---|---|
| Polyacrylamide | 8.0 |
| Malto Dextrin | 6.5 |
| Pectin | 4.0 |
| Glycerin | 49.8 |
| Propylene Glycol | 7.6 |
| Water | 7.0 |
| Adhesive | 15.0 |
| Salicylic Acid | 0.5 |
| Skin Conditioners | 1.6 |

EXAMPLE 18

Specific Therapeutic Formulation

| Component | Weight % |
|---|---|
| Polyacrylamide | 13.0 |
| Karaya | 6.0 |
| Malto Dextrin | 4.5 |
| Pectin | 2.0 |
| Glycerin | 47.0 |
| Propylene Glycol | 6.6 |
| Water | 7.4 |
| Adhesive | 8.0 |
| Salicylic Acid | 0.5 |
| Skin Conditioners | 5.0 |

EXAMPLE 19

Specific Therapeutic Formulation

| Component | Weight % |
|---|---|
| Polyacrylamide | 16.0 |
| Malto Dextrin | 6.5 |
| Pectin | 4.0 |
| Glycerin | 49.0 |
| Propylene Glycol | 6.6 |
| Water | 5.6 |
| Adhesive | 10.0 |
| Salicylic Acid | 0.5 |
| Skin Conditioners | 1.8 |

EXAMPLE 20

Specific Therapeutic Formulation

| Component | Weight % |
|---|---|
| polyacrylamide | 18.0 |
| Malto Dextrin | 8.0 |
| Pectin | 6.0 |
| Glycerin | 40.0 |
| Propylene Glycol | 6.2 |
| Water | 5.6 |
| Adhesive | 14.0 |
| Salicylic Acid | 0.2 |
| Skin Conditioners | 2.0 |

EXAMPLE 21

Specific Therapeutic Formulation

| Component | Weight % |
|---|---|
| Polyacrylamide | 9.0 |
| Malto Dextrin | 5.0 |
| Pectin | 4.0 |
| Glycerin | 47.8 |
| Propylene Glycol | 6.6 |
| Water | 12.0 |
| Adhesive | 8.0 |
| Salicylic Acid | 5.0 |
| Skin Conditioners | 2.6 |

EXAMPLE 22

Specific Therapeutic Formulation

| Component | Weight % |
|---|---|
| Polyacrylamide | 16.0 |
| Malto Dextrin | 3.0 |
| Pectin | 2.0 |
| Glycerin | 46.5 |
| Propylene Glycol | 5.6 |
| Water | 8.1 |
| Adhesive | 10.0 |
| Salicylic Acid | 7.0 |
| Skin Conditioners | 1.8 |

EXAMPLE 23

Specific Therapeutic Formulation

| Component | Weight % |
|---|---|
| Karaya | 10.0 |
| Malto Dextrin | 8.0 |
| Pectin | 5.0 |
| Glycerin | 42.0 |
| Propylene Glycol | 8.4 |
| Water | 7.6 |
| Adhesive | 9.0 |
| Salicylic Acid | 7.5 |
| Skin Conditioners | 2.5 |

EXAMPLE 24

Specific Therapeutic Formulation

| Component | Weight % |
|---|---|
| Polyacrylamide | 12.0 |
| Malto Dextrin | 7.5 |
| Pectin | 4.0 |
| Glycerin | 46.4 |
| Propylene Glycol | 6.9 |
| Water | 5.6 |
| Adhesive | 12.2 |
| Resorcinol | 3.0 |
| Skin Conditioners | 2.4 |

EXAMPLE 25

Specific Therapeutic Formulation

| Component | Weight % |
|---|---|
| Polyacrylamide | 13.0 |
| Malto Dextrin | 5.0 |
| Pectin | 4.0 |
| Glycerin | 45.6 |
| Propylene Glycol | 9.6 |
| Water | 7.0 |
| Adhesive | 7.0 |
| Sulfur | 7.0 |
| Skin Conditioners | 1.8 |

EXAMPLE 26

Specific Therapeutic Formulation

| Component | Weight % |
|---|---|
| Polyacrylamide | 17.0 |
| Malto Dextrin | 6.0 |
| Pectin | 6.0 |
| Glycerin | 46.6 |
| Ethylene Glycol | 9.6 |
| Water | 4.0 |
| Adhesive | 2.0 |
| Salicylic Acid | 2.0 |
| Skin Conditioners | 6.8 |

EXAMPLE 27

Specific Therapeutic Formulation

| Component | Weight % |
|---|---|
| Polyacrylamide | 8.0 |
| Malto Dextrin | 7.0 |
| Pectin | 6.0 |
| Glycerin | 48.0 |
| Propylene Glycol | 4.6 |
| Ethylene Glycol | 6.2 |
| Water | 8.0 |
| Adhesive | 6.0 |
| Salicylic Acid | 2.0 |
| Skin Conditioners | 4.2 |

EXAMPLE 28

Specific Therapeutic Formulation

| Component | Weight % |
|---|---|
| Polyacrylamide | 12.0 |
| Malto Dextrin | 7.0 |
| Pectin | 4.0 |
| Glycerin | 47.4 |
| Propylene Glycol | 5.6 |
| Water | 5.6 |
| Adhesive | 13.0 |
| Salicylic Acid | 2.0 |
| Tetracycline | 1.0 |
| Skin Conditioners | 2.4 |

EXAMPLE 29

Specific Therapeutic Formulation

| Component | Weight % |
|---|---|
| Karaya | 18.0 |
| Malto Dextrin | 5.0 |
| Pectin | 3.0 |
| Glycerin | 41.0 |
| Propylene Glycol | 8.0 |
| Water | 7.6 |
| Adhesive | 13.0 |
| Salicylic Acid | 2.0 |
| Triclosan | 0.4 |
| Skin Conditioners | 2.0 |

EXAMPLE 30

Specific Therapeutic Formulation

| Component | Weight % |
|---|---|
| Polyacrylamide | 17.0 |
| Malto Dextrin | 3.0 |
| Pectin | 2.0 |
| Glycerin | 46.5 |
| Propylene Glycol | 8.6 |
| Water | 8.1 |
| Adhesive | 10.0 |
| Benzoyl peroxide | 1.0 |
| Skin Conditioners | 3.8 |

EXAMPLE 31

Specific Therapeutic Formulation

| Component | Weight % |
| --- | --- |
| Polyacrylamide | 16.0 |
| Malto Dextrin | 5.2 |
| Pectin | 4.2 |
| Glycerin | 50.0 |
| Propylene Glycol | 6.6 |
| Water | 6.0 |
| Adhesive | 10.0 |
| Salicylic Acid | 2.0 |

EXAMPLE 32

Yield Improvement Data

A. Non-woven Backing not Treated with a Sizing Agent

The adhesive patch was produced by mixing the ointment or gel of Example 1 in a mixer, then expelling the ointment or gel in a fluid state from the mixer onto the exposed front surface of a N7601 non-woven backing sheet, which is commercially available from Dexter Nonwovens (Windsor Locks, Conn.). The fluid ointment or gel was then spread over the exposed surface of the backing sheet using an appropriate direct coating technique, such as knife-over-roll. All of the material that was produced had an unacceptably tacky surface on the back side of the backing. As such, the yield was 0% of the theoretical amount of product obtained.

B. Non-woven Backing Treated with a Sizing Agent

The adhesive patch was produced by mixing the ointment or gel of Example 1 in a mixer, then expelling the ointment or gel in a fluid state from the mixer onto the exposed front surface of a Vilmed M 1585 W/HY non-woven backing sheet that is pre-treated with a fluorocarbon. The pre-treated non-woven backing sheet is commercially available from Freudenberg Faservliesstoffe KG (Weinham, Germany). The fluid ointment or gel was then spread over the exposed surface of the backing sheet using an appropriate direct coating technique, such as knife-over-roll. The yield rate was 88% of the theoretical amount of product obtained.

The adhesive patch 1 of the present invention can be formulated or manufactured employing the above components. The adhesive patch 1 of the present invention can be formulated or manufactured using any suitable technique. Preferably, the adhesive patch 1 can be formulated or manufactured as described herein or as described in U.S. Pat. No. 5,536,263; U.S. Pat. No. 5,741,510; and references cited therein; wherein the oil premix includes the topical acne drug 15, propylene glycol, and solvent 13; the glycerin premix includes glycerin, Vitamin E, and aloe vera gel; and the adhesive premix includes the adhesive, polymer 9, and water; and wherein the backing is treated with a hydrophobic sizing agent 8 prior to the infusion of the therapeutic formulation 5.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An adhesive patch comprising a flexible backing having a front side and a back side and a therapeutic formulation positioned on at least a portion of the front side of the backing, in at least a portion of the front side of the backing, or on and in at least a portion of ti front side of the backing; wherein at least a portion of the backing is treated with a hydrophobic sizing agent that is a silicone-containing compound selected from the group polydimethyl siloxanes, dialkylsiloxanes, dimnethylsiloxo vinyl alkenes, dialkylsiloxo vinyl alkenes, dimethylsiloxo acrylates, dialky siloxo acrylates, vinyl terminated polydinethylsiloxanes, and vinyl terminated polydialkylsiloxanes; wherein the therapeutic formulation comprises:

a topical acne drug;

a solvent that dissolves the topical acne drug; and a pressure sensitive adhesive.

2. The adhesive patch of claim 1 wherein the therapeutic formulation is partially embedded in at least a portion of the front side of the backing.

3. The adhesive patch of claim 1 wherein the therapeutic formulation is located on the entire surface of the front side of the backing.

4. The adhesive patch of claim 1 wherein the backing is porous.

5. The adhesive patch of claim 1 wherein the backing is vapor permeable.

6. The adhesive patch of claim 1 wherein the backing comprises water insoluble material.

7. The adhesive patch of claim 1 wherein the backing has a thickness of about 0.025 mm to about 1.25 mm.

8. The adhesive patch of claim 1 wherein the backing comprises a nonwoven fabric.

9. The adhesive patch of claim 1 wherein the hydrophobic sizing agent has a surface energy of about 20 dynes/cm$^2$ to about 65 dynes/cm$^2$.

10. The adhesive patch of claim 1 wherein the backing is nonwoven fabric.

11. The adhesive patch of claim 1 wherein the hydrophobic sizing agent is a silicone-containing compound selected from the group polydinmethyl siloxane, a dialkylsiloxane, a dimethylsiloxo vinyl alkene, a dialkylsiloxo vinyl alkene, a dimethylsiloxo acrylate, a dialkylsiloxo acrylate, and a combination thereof.

12. The adhesive patch of claim 1 wherein at least a portion of the front side of the backing is treated with the sizing agent.

13. The adhesive patch of claim 1 wherein the entire surface of the front side of the backing is treated with the sizing agent.

14. The adhesive patch of claim 1 wherein the entire backing is treated with the sizing agent.

15. The adhesive patch of claim 1 wherein the sizing agent is partially embedded in the backing.

16. The adhesive patch of claim 1 wherein the backing comprises polycellulose fibers, polyester fibers, polyurethane fibers, polyolefin fibers, polyamide fibers, cotton fibers, copolyester fibers, or any mixture thereof.

17. The adhesive patch of claim 1 wherein upon contact with skin, the backing retains the therapeutic formulation and the patch allows moisture from the skin to pass.

18. The adhesive patch of claim 1 wherein the topical acne drug is salicylic acid, resorcinol, resorcinol acetate, benzoyl peroxide, sulfur, retinol, retinoic acid, citric acid, an alpha hydroxy acid, retinal, a pharmaceutically acceptable salt thereof, or any combination thereof.

19. The adhesive patch of claim 1 wherein the topical acne drug is salicylic acid or a pharmaceutically acceptable salt thereof.

20. The adhesive patch of claim 19 wherein the salicylic acid or the pharmaceutically acceptable salt thereof is present in about 0.5 wt. % to about 2.0 wt. % of the therapeutic formulation.

21. The adhesive patch of claim 18 wherein the sulfur is present in about 3.0 wt. % to about 10.0 wt. % of the therapeutic formulation.

22. The adhesive patch of claim 1 wherein the solvent comprises a polyhydric alcohol, water, or a combination thereof.

23. The adhesive patch of claim 22 wherein the polyhydric alcohol is propylene glycol, ethylene glycol, or a combination thereof.

24. The adhesive patch of claim 23 wherein the propylene glycol is present in about 3.0 wt. % to about 11.0 wt. % of the therapeutic formulation.

25. The adhesive patch of claim 22 wherein the water is present in about 2.0 wt. % to about 20.0 wt. % of the therapeutic formulation.

26. The adhesive patch of claim 1 wherein the solvent is present in about 6.0 wt. % to about 24.0 wt. % of the therapeutic formulation.

27. The adhesive patch of claim 1 wherein the therapeutic formulation further comprises a filler.

28. The adhesive patch of claim 27 wherein the filler is malto dextrin.

29. The adhesive patch of claim 28 wherein the malto dextrin is present in about 1.0 wt. % to about 10.0 wt. % of the therapeutic formulation.

30. The adhesive patch of claim 1 wherein the pressure sensitive adhesive comprises one or more acrylic ester copolymers.

31. The adhesive patch of claim 30 wherein the one or more acrylic ester copolymers are present in about 3.0 wt. % to about 20.0 wt. % of the therapeutic formulation.

32. The adhesive patch of claim 30 wherein the acrylic ester copolymer is present in about 5.0 wt. % to about 15.0 wt. % of the therapeutic formulation.

33. The patch of claim 1 wherein the adhesive is positioned on the entire front side of the backing.

34. The patch of claim 1 wherein the adhesive is positioned on a portion of front side of the backing.

35. The patch of claim 1 wherein the adhesive is partially embedded in at least a portion of the backing.

36. The adhesive patch of claim 1 wherein the pressure sensitive adhesive further comprises glycerin.

37. The adhesive patch of claim 36 wherein the glycerin is present in about 25.0 wt. % to about 70.0 wt. % of the therapeutic formulation.

38. The adhesive patch of claim 36 wherein the glycerin is present in about 45.0 wt. % to about 55.0 wt. % of the therapeutic formulation.

39. The adhesive patch of claim 1 wherein the pressure sensitive adhesive comprises an emulsifier.

40. The adhesive patch of claim 39 wherein the emulsifier is pectin.

41. The adhesive patch of claim 40 wherein the pectin is present in about 2.0 wt. % to about 10.0 wt. % of the therapeutic formulation.

42. The adhesive patch of claim 1 wherein the pressure sensitive adhesive comprises a compound that provides structure and strength to the pressure sensitive adhesive or to the therapeutic formulation.

43. The adhesive patch of claim 42 wherein the compound that provides structure and strength to the pressure sensitive adhesive or to the therapeutic in formulation is karaya, a polyacrylamide, xanthum gum, guar gum, a natural polymer, a synthetic polymer, a hydrophilic polymer, a hydrocolloidal polymer, starch, a starch derivative, vinyl acetate copolymer, polyvinyl pyrrolidone, polyethylene oxide, algin, derivatives of algin, a polyacrylate, polymaleic acid, polymaleic anhydride, a polyurethane, a polyurea, gum acacia, locust bean gum, modified guar gum, maltodextrin, carboxymethyl cellulose, carboxypropyl cellulose, polyvinyl alcohol, poly AMPS or a mixture thereof.

44. The adhesive patch of claim 42 wherein the compound that provides structure and strength to the pressure sensitive adhesive or to the therapeutic formulation is polyacrylamide.

45. The adhesive patch of claim 44 wherein the polyacrylamide is present in about 8.0 wt. % to about 30.0 wt. % of the therapeutic formulation.

46. The adhesive patch of claim 42 wherein the compound that provides structure and strength to the pressure sensitive adhesive or to the therapeutic formulation is karaya.

47. The adhesive patch of claim 46 wherein the karaya is present in about 8.0 wt. % to about 40.0 wt. % of the therapeutic formulation.

48. The adhesive patch of claim 42 wherein the compound that provides structure and strength to the pressure sensitive adhesive or to the therapeutic formulation is a combination of polyacrylamide and karaya.

49. The adhesive patch of claim 1 wherein the pressure sensitive adhesive is located on the entire portion of the front side of the backing.

50. The adhesive patch of claim 1 wherein the therapeutic formulation further comprises a skin conditioner.

51. The adhesive patch of claim 50 wherein the skin conditioner is calamine, aloe, lanolin, glycerin, Vitamin E, Vitamin E acetate, famesol, glycyrrhetinic acid, or any combination thereof.

52. The adhesive patch of claim 51 wherein the aloe is present in about 0.01 wt. % to about 2.0 wt. % of the therapeutic formulation.

53. The adhesive patch of claim 51 wherein the Vitamin E acetate is present in about 0.01 wt. % to about 2.0 wt. % of the therapeutic formulation.

54. The adhesive patch of claim 1 wherein the therapeutic formulation further comprises one or more antimicrobial agents.

55. The adhesive patch of claim 54 wherein the antimicrobial agent is a β-lactam compound, an aminoglycoside, or an antifungal agent.

56. The adhesive patch of claim 54 wherein the antimicrobial agent is erythromycin, tetracycline, clindamycin, or cephalosporin.

57. The adhesive patch of claim 1 wherein the therapeutic formulation further comprises one or more antiseptic agents.

58. The adhesive patch of claim 57 wherein the antiseptic agent is triclosan, phenoxy isopropanol, chlorhexidine gluconate, povidone iodine, or any combination thereof.

59. The adhesive patch of claim 1 having a thickness of about 0.20 mm to about 0.75 mm.

60. The adhesive patch of claim 1 further comprising a release liner that is mounted on the front side of the backing.

61. The adhesive patch of claim 60 wherein more than one patch is mounted on the release liner.

62. The adhesive patch of claim 61 wherein about 2 to about 20 adhesive patches are mounted on the release liner.

63. The adhesive patch of claim 1 that is crescent, circular, or oval.

64. The adhesive patch of claim 63 having a diameter of about 0.1 inch to about 1.0 inch.

65. The adhesive patch of claim 1 wherein the portion of the backing treated with the hydrophobic sizing agent has a surface energy of about 27 dynes/cm$^2$ to about 56 dynes/cm$^2$.

66. The adhesive patch of claim 1 wherein the entire surface of the backing is treated with the hydrophobic sizing agent.

67. The adhesive patch of claim 1 wherein the hydrophobic sizing agent penetrates at least a portion of the underlying surface of the backing.

68. The adhesive patch of claim 1 wherein the hydrophobic sizing agent penetrates the entire underlying surface of the backing.

69. An adhesive patch comprising a flexible backing having a front side and a back side and a therapeutic formulation positioned on at least a portion of the front side of the back, in at least a portion of the front side of the backing, or on and in at least a portion of the front side of the backing; wherein at least a portion of the backing is treated with a hydrophobic sizing agent such that the portion of the backing treated with the hydrophobic sizing agent that is a silicone-containing compound selected from the group polydimethyl siloxanes, dialkylsiloxane, dimethylsiloxo vinyl alkenes, diallylsiloxo vinyl alkenes, dimethylsiloxo acrylates, dialkylsiloxo acrylates, vinyl terminated polydimethylsiloxanes, and vinyl terminated polydialkylsiloxanes; wherein the therapeutic formulation comprises:

salicylic acid or a pharmaceutically acceptable salt thereof present in about 0.5 wt. % to about 2.0 wt. % of the therapeutic formulation;

a solvent that dissolves the salicylic acid; and a pressure sensitive adhesive.

70. An adhesive patch comprising a flexible backing having a front side and a back side and a therapeutic formulation positioned on at least a portion of the front side of the backing, in at least a portion of the front side of the baking, or on and in at least a portion of the front side of the backing; wherein at least a portion of the backing is treated with a hydrophobic sizing agent such that the portion of the backing that is treated with the hydrophobic sizing agent that is a silicone-containing compound selected from the group polydimethyl siloxanes, dilylsiloxanes, dimethyisiloxo vinyl alkenes, dialkylsiloxo vinyl alkenes, dimethylsiloxo acrylates, dialkylsiloxo acrylates, vinyl terminated polydimethylsiloxanes, and vinyl terminated polydialkylsiloxanes; wherein the therapeutic formulation comprises:

a topical acne drug, and a hot melt adhesive.

71. A method for treating or preventing acne or a pimple in a mammal in need thereof comprising applying to the skin surface of the mammal having the acne or the pimple or the skin surface of the mammal at risk thereof an adhesive patch of any one of claims 1, 69, or 70 for an effective period of time to effectively treat or prevent acne or a pimple.

72. The method of claim 71 wherein the mammal is a human.

73. The method of claim 71 wherein the skin surface of the mammal having the acne or pimple or the skin surface of the mammal at risk thereof is the face, neck, shoulder, chest, back, or any combination thereof.

74. The method of claim 71 wherein the period of time is about one hour to about 12 hours.

75. A method for exfoliating the skin surface of a mammal comprising applying to the skin surface of the mammal in need of such exfoliating an adhesive patch of any one of claims 1, 69, or 70 for an effective period of time and removing the adhesive patch, thereby effectively exfoliating the skin surface.

76. The method of claim 75 wherein the mammal is a human.

77. The method of claim 75 wherein the effective period of time is about one second to about 12 hours.

\* \* \* \* \*